United States Patent [19]
Thomas et al.

[11] Patent Number: 5,977,436
[45] Date of Patent: Nov. 2, 1999

[54] OLEOSIN 5' REGULATORY REGION FOR THE MODIFICATION OF PLANT SEED LIPID COMPOSITION

[75] Inventors: Terry L. Thomas; Zhongsen Li, both of College Station, Tex.

[73] Assignee: Rhone Poulenc Agrochimie, Lyons, France

[21] Appl. No.: 08/831,575

[22] Filed: Apr. 9, 1997

[51] Int. Cl.$^6$ ............................. A01H 5/00; C12N 15/29; C12N 15/82; C12P 7/64

[52] U.S. Cl. ........................ 800/281; 800/278; 800/286; 800/287; 800/288; 800/298; 800/307; 800/312; 800/314; 800/317.3; 800/320.1; 800/322; 536/23.6; 536/24.1; 435/69.1; 435/252.3; 435/320.1; 435/419; 435/468

[58] Field of Search ............................... 435/69.1, 172.3, 435/320.1, 419, 468, 252.3; 536/24.1, 23.6; 800/205, DIG. 14, DIG. 15, DIG. 17, DIG. 26, DIG. 27, DIG. 43, DIG. 56, DIG. 69, 278, 281, 287, 288, 286, 298, 307, 312, 314, 317.3, 320.1, 322

[56] References Cited

U.S. PATENT DOCUMENTS

| | | | |
|---|---|---|---|
| 5,365,015 | 11/1994 | Grierson et al. | 800/205 |
| 5,552,306 | 9/1996 | Thomas et al. | 435/134 |
| 5,614,393 | 3/1997 | Thomas et al. | 435/134 |

FOREIGN PATENT DOCUMENTS

| | | |
|---|---|---|
| WO 93 11245 | 6/1993 | WIPO . |
| WO 93 20216 | 10/1993 | WIPO . |
| WO 94 11516 | 5/1994 | WIPO . |
| WO 94 18337 | 8/1994 | WIPO . |
| WO 96 06936 | 3/1996 | WIPO . |
| WO 96 21022 | 7/1996 | WIPO . |
| WO 96 23892 | 8/1996 | WIPO . |

OTHER PUBLICATIONS

Li, et al. (1997) "Isolation and Characterization of Arabidopsis Embryo–Specific Genes (Virtual Subtraction, DNA Binding Sites, Gene Isolation)", Ph.D. thesis, Texas A&M University, 107–128.

Beremand, P.D., et al. (1997) "Production of Gamma–linolenic Acid by Transgenic Plants Expressing Cyanobacterial or Plant Delta6–desaturase Genes", *Proc. Int. Symp. Plant Lipids.*, 12th: 351–353.

Kirik, et al. (1996) "Two New Oleosin Isoforms With Altered Expression Patterns in Seeds of the Arabidopsis Mutant fus3", *Plant Molecular Biology*, 31:413–417.

Töpfer, et al. (1995) "Modification of Plant Lipid Synthesis", *Science*, 268:681–686.

Gibson, et al. (1994) "Cloning of a Temperature–regulated Gene Encoding a Chloroplast Omega–3 Desaturase from *Arabidopsis thaliana*", *Plant Physiol.*, 104: 1615–1621.

Plant, et al. (1994) "Regulation of an Arabidopis Oleosin Gene Promoter in Transgenic *Brassica Napus*", *Plant Molecular Biology*, 25:193–205.

Smith et al. Antisense RNA inhibition of polygalacturonase gene expression in transgenic tomatoes. Nature. 334:724–726, Aug. 1988.

Napoli et al. Introduction of a chimeric chalcone synthase gene into petunia results in reversible co–suppression of homologous genes in trans. The Plant Cell. 2:270–289, Apr. 1990.

Plant et al. Regulation of an Arabidopsis oleosin gene promoter in transgenic *Brassica napus*. Plant Molecular Biology. 25:193–205, 1994.

Reddy et al. Isolation of a delta–6–desaturase gene from the cyanobacterium Synechocystis sp. strain PCC 6803 by gain–of–function expression in Anabaena sp. strain PCC 7120. Plant Molecular Biology. 27:293–300, May 1993.

Reddy et al. Expression of a Cyanobacterial delta–6–desaturase gene results in a gamma–linolenic acid production in transgenic plants. Nature Biotechnology. 14:639–642, May 1996.

Allen, et al. (1987) "Sequence and Expression of a Gene Encoding An Albumin Storage Protein in Sunflower", *Mol. Gen. Genet.*, 210:211–218.

Allen, et al. (1985) "Developmental Expression of Sunflower 11S Storage Protein Genes", *Plant Molecular Biology*, 5:165–173.

Bechtold, et al. (1993) "In Planta Agrobacterium Mediated Gene Transfer by Infiltration of Adult *Arabidopsis thaliana* Plants", *C.R. Acad. Sci. Paris*, 316:1194–1199.

Bogue, et al. (1990) "Developmentally Regulated Expression of a Sunflower 11S Seed Protein Gene in Transgenic Tobacco", *Mol. Gen. Genet.*, 221:49–57.

Brenner, R.R. (1976) "Regulatory Function of Δ6 Desaturase—Key Enzyme of Polyunsaturated Fatty Acid Synthesis", *Adv. Exp. Med. Biol.*, 83:85–101.

Cahoon, et al. (1992) "Expression of a Coriander Desaturase Results in Petroselinic Acid Production in Transgenic Tobacco", *Proc. Natl. Acad. Sci USA*, 89:11184–11188.

Chang, et al. (1993) "A Simple and Efficient Method for Isolating RNA from Pine Trees", *Plant Mol. Biol. Rep.*, 11:113–116.

Crouch, et al. (1983) "cDNA Clones for *Brassica napus* Seed Storage Proteins: Evidence from Nucleotide Sequence Analysis that Both Subunits of Napin are Cleaved from a Precursor Polypeptide", *J. Mol. Appl. Genet.*, 2:273–284.

(List continued on next page.)

*Primary Examiner*—David T. Fox
*Attorney, Agent, or Firm*—Scully, Scott, Murphy & Presser

[57] ABSTRACT

The present invention is directed to 5' regulatory regions of an Arabidopsis oleosin gene. The 5' regulatory regions, when operably linked to either the coding sequence of a heterologous gene or a sequence complementary to a native plant gene, direct expression of the coding sequence or complementary sequence in a plant seed. The regulatory regions are useful in expression cassettes and expression vectors for the transformation of plants. Also provided are methods of modulating the levels of a heterologous gene such as a fatty acid synthesis or lipid metabolism gene by transforming a plant with the subject expression cassettes and expression vectors.

28 Claims, 20 Drawing Sheets

OTHER PUBLICATIONS

Dahmer, et al. (1989) "A Rapid Screening Technique for Determining the Lipid Composition of Soybean Seeds", *J. Amer. Oil. Chem. Soc.,* 66: 543–548.

Ericson, et al. (1986) "Structure of the Rapeseed 1.7 S Storage Protein, Napin, and Its Precursor", *J. Biol. Chem.,* 261:14576–14581.

Higgins, et al. (1986) "Gene Structure, Protein Structure, and Regulation of the Synthesis of a Sulfur–rich Protein in Pea Seeds", *J. Biol. Chem,* 261:11124–11130.

Higgins, et al. (1987) "cDNA and Protein Sequence of a Major Pea Seed Albumin (PA 2:$M_2$ ~ 26 000)", *Plant Mol. Biol.,* 8:37–45.

Horsch, et al. (1985) "A Simple and General Method for Transferring Genes into Plants", *Science,* 227:1229–1231.

Huang, A.H.C. (1992) "Oil Bodies and Oleosins in Seeds", *Ann. Reviews Plant Phys. and Plant Mol. Biol.,* 43:177–200.

Jefferson, et al. (1987) "GUS fusions: β–Glucuronidase as a Sensitive and Versatile Gene Fusion Marker in Higher Plants", *EMBO J.,* 6:3901–3907.

Larkins, et al. (1975) "Polyribosomes from Peas", *Plant Phys.,* 55: 749–756.

Laroche–Raynal, et al. (1986) Identification and Characterization of the mRNA for Major Storage Proteins from Radish, *Eur. J. Biochem.,* 157:321–327.

Mechler (1987) "Isolation of Messenger RNA from Membrane–Bound Polysomes", *Methods in Enzymology,* 152: 241–248, Academic Press.

Napoli, et al. (1990) "Introduction of a Chimeric Chalcone Synthase Gene into Petunia Results in Reversible Co–Suppression of Homologous Genes in Trans", *The Plant Cell,* 2:270–289.

Ohlrogge, et al. (1991) "The Genetics of Plant Lipids", *Biochim. et Biophys. Acta,* 1082:1–26.

Ohlrogge, J.B. (1994) "Design of New Plant Products: Engineering of Fatty Acid Metabolism", *Plant Physiol.,* 104:821–826.

Plant, et al. (1994) "Regulation of an Arabidopsis Oleosin Gene Promoter in Transgenic *Brassica Napus*", *Plant Mol. Biol.,* 25:193–205.

Reddy, et al. (1996) "Expression of a Cyanobacterial Δ6–Desaturase Gene Results in a γ–Linolenic Acid Production in Transgenic Plants", *Nature Biotech.,* 14:639–642.

Schmidt, et al. (1994) Purification of PCR–based cDNA cloning of a Plastidial n–6 Desaturase:, *Plant Mol. Biol.,* 26:631–642.

Sun, et al. (1987) "Properties, Biosynthesis and Processing of a Sulfur–Rich Protein in a Brazil Nut (*Bertholletia excelsa* H.B.K.)", *Eur. J. Bioch.,* 162:477–483.

Töpfer, et al. (1995) Modification of Plant Lipid Synthesis, *Science,* 268:681–686.

Van de Loo, et al. (1995) "An Oleate 12–Hydroxylase from *Ricinus communis* L. is a Fatty Acyl Desaturase homolog", *Proc. Natl. Acad. Sci USA,* 92:6743–6747.

Van der Krol, et al. (1990) "Flavonoid Genes in Petunia: Addition of a Limited Number of Gene Copies May Lead to a Suppression of Gene Expression", *The Plant Cell,* 2:291–299.

Van Rooijen, et al. (1992) "Nucleotide Sequence of an *Arabidopsis thaliana* Oleosin Gene", *Plant Mol. Biol.,* 18:1177–1179.

Vance, et al. (1987) "The Major Protein From Lipid Bodies of Maize", *J. Biol. Chem.,* 262:11275–11279.

Weete, J.D. (1980) "Lipid Biochemistry of Fungi and Other Organisms", eds. Plenum Press, New York, pp. 59–62.

Youle, et al. (1981) "Occurrence of Low Molecular Weight and High Cysteine Containing Albumin Storage Proteins in Oilseeds of Diverse Species", *Amer. J. Bot.,* 68:44–48.

Zou, et al.(1996) "Cloning of a cDNA Encoding the 21.2 kDa Oleosin Isoform from *Arabidopsis thaliana* and a Study of Its Expression in a Mutant Defective in Diacylglycerol Acyltransferase Activity", *Plant Mol.Biol.,* 31:429–433.

FIG.1A

```
  2 ata tct gcc tac cct ccc aaa gag agt agt cat ttt tca atg gct gct caa atc aag
     I   S   A   Y   P   P   K   E   S   S   H   F   S   M   A   A   Q   I   K 62 aaa tac att acc tca gat gaa ctc aag aac cac gat aaa ccc gga gat cta tgg atc tcg
     K   Y   I   T   S   D   E   L   K   N   H   D   K   P   G   D   L   W   I   S 122 att caa ggg aaa gcc tat gat gtt tcg gat tgg gtg aaa gac cat cca ggt ggc agc ttt
     I   Q   G   K   A   Y   D   V   S   D   W   V   K   D   H   P   G   G   S   F 182 ccc ttg aag agt ctt gct ggt caa gag gta act gat gca ttt gtt gca ttc cat cct gcc
     P   L   K   S   L   A   G   Q   E   V   T   D   A   F   V   A   F   H   P   A 242 tct aca tgg aag aat ctt gat aag ttt ttc act ggg tat tat ctt aaa gat tac tct gtt
     S   T   W   K   N   L   D   K   F   F   T   G   Y   Y   L   K   D   Y   S   V 302 tct gag gtt tct aaa gat tat agg aag ctt gtg ttt gag ttt tct aaa atg ggt ttg tat
     S   E   V   S   K   D   Y   R   K   L   V   F   E   F   S   K   M   G   L   Y 362 gac aaa aaa ggt cat att atg ttt gca act ttg tgc ttt ata gca atg ctg ttt gct atg
     D   K   K   G   H   I   M   F   A   T   L   C   F   I   A   M   L   F   A   M
```

FIG. 1B

```
422
agt gtt tat ggg gtt ttg ttt tgt gag ggt gtt ttg gta cat ttg ttt tct ggg tgt ttg
 S   V   Y   G   V   L   F   C   E   G   V   L   V   H   L   F   S   G   C   L 482
atg ggg ttt ctt tgg att cag agt ggt tgg att gga cat gat gct ggg cat tat atg gta
 M   G   F   L   W   I   Q   S   G   W   I   G   H   D   A   G   H   Y   M   V 542
gtg tct gat tca agg ctt aat aag ttt atg ggt att ttt gct gca aat tgt ctt tca gga
 V   S   D   S   R   L   N   K   F   M   G   I   F   A   A   N   C   L   S   G 602
ata agt att ggt tgg tgg aaa tgg aac cat aat gca cat cac att gcc tgt aat agc ctt
 I   S   I   G   W   W   K   W   N   H   N   A   H   H   I   A   C   N   S   L 662
gaa tat gac cct gat tta caa tat ata cca ttc ctt gtt gtg tct tcc aag ttt ttt ggt
 E   Y   D   P   D   L   Q   Y   I   P   F   L   V   V   S   S   K   F   F   G 722
tca ctc acc tct cat ttc tat gag aaa agg ttg act ttt gac tct tta tca aga ttc ttt
 S   L   T   S   H   F   Y   E   K   R   L   T   F   D   S   L   S   R   F   F
```

FIG.1C

```
782
gta agt tat caa cat tgg aca ttt tac cct att atg tgt gct agg ctc aat atg tat
 V   S   Y   Q   H   W   T   F   Y   P   I   M   C   A   A   R   L   N   M   Y
842
gta caa tct ctc ata atg ttg ttg acc aag aga aat gtg tcc tat cga gct cag gaa ctc
 V   Q   S   L   I   M   L   L   T   K   R   N   V   S   Y   R   A   Q   E   L
902
ttg gga tgc cta gtg ttc tcg att tgg tac ccg ttg ctt gtt tct tgt ttg cct aat tgg
 L   G   C   L   V   F   S   I   W   Y   P   L   L   V   S   C   L   P   N   W
962
ggt gaa aga att atg ttt gtt att gca agt tta tca gtg act gga atg caa caa gtt cag
 G   E   R   I   M   F   V   I   A   S   L   S   V   T   G   M   Q   Q   V   Q
1022
ttc tcc ttg aac cac ttc tct tca agt gtt tat gtt gga aag cct aaa ggg aat aat tgg
 F   S   L   N   H   F   S   S   S   V   Y   V   G   K   P   K   G   N   N   W
1082
ttt gag aaa caa acg gat ggg aca ctt gac att tct tgt cct cct tgg atg gat tgg ttt
 F   E   K   Q   T   D   G   T   L   D   I   S   C   P   P   W   M   D   W   F
```

FIG.1D

```
1142
cat ggt gga ttg caa ttc caa att gag cat cat ttg ttt ccc aag atg cct aga tgc aac
 H   G   G   L   Q   F   Q   I   E   H   H   L   F   P   K   M   P   R   C   N 1202
ctt agg aaa atc tcg ccc tac gtg atc gag tta tgc aag aaa cat aat ttg cct tac aat
 L   R   K   I   S   P   Y   V   I   E   L   C   K   K   H   N   L   P   Y   N 1262
tat gca tct ttc tcc aag gcc aat gaa atg aca ctc aga aca ttg agg aac aca gca ttg
 Y   A   S   F   S   K   A   N   E   M   T   L   R   T   L   R   N   T   A   L 1322
cag gct agg gat ata acc aag ccg ctc ccg aag aat ttg gta tgg gaa gct ctt cac act
 Q   A   R   D   I   T   K   P   L   P   K   N   L   V   W   E   A   L   H   T 1382
cat ggt taa aat tac cct tag ttc atg taa taa ttt gag att atg tat ctc cta tgt ttg
 H   G   *

1442
tgt ctt gtc ttg gtt cta ctt gtt gga gtc att gca act tgt ctt tta tgg ttt att aga 1502
tgt ttt tta ata tat ttt aga ggt ttt gct ttc atc tcc att att gat gaa taa gga gtt
```

FIG.1E

```
1562
gca tat tgt caa ttg ttg tgc tca ata tct gat att ttg gaa tgt act ttg tac cac tgt 1622
gtt ttc agt tga agc tca tgt gta ctt cta tag act ttg ttt aaa tgg tta tgt cat gtt 1682
att t
```

FIG. 3A
FIG. 3B
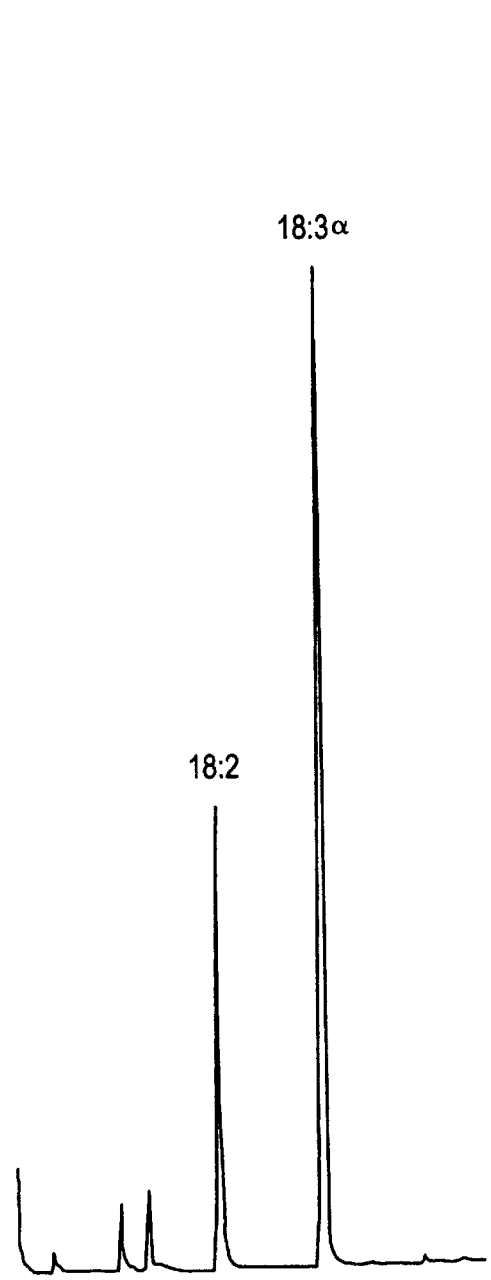
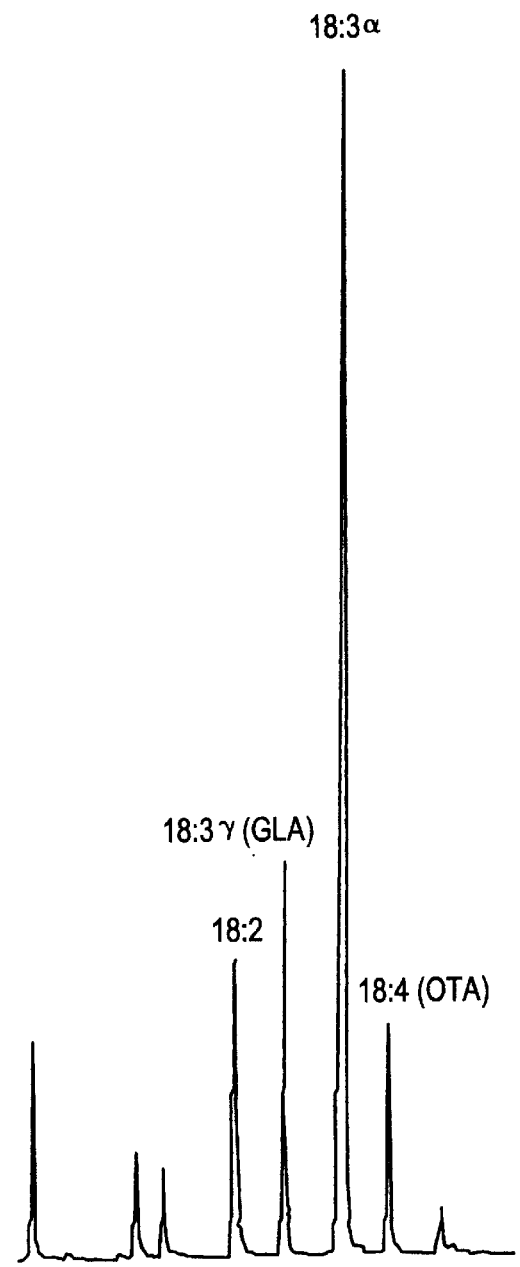

```
AtS21    MANVDRDRRV HVDRTDKRVH           -QPNYEDDVG ---F-G--GY GGYGAGSDYK  43
X91918   MANVDRDRRV HVDRTDKRVH           -QPNYEDDVG ---F-G--GY GGYGAGSDYK  43
Z29859   ---------- ----------           ---------- ---------- ----------
X62352   MADTARG--- -THHDIIGRD           QYPMMGRDRD QYQKSGRG-- ------SDY-  37
Atol3    MADQTR---- -THHE-----           ---MISRDST Q--------- ------EAH-  21
X91956   MADTHR---- -VDRTDRHFQ           FQSPYEGGRG QGQYEGDRGY GGGGYKSMMP  45
L40954   MADTHR---- -VDRTDRHFQ           FQSPYEGGRG QGQYEGDRGY GGGGYKSMMP  45

AtS21    SRGPSTNQIL ALIAGVPIGG  TLITLAGLTL AGSVIGLIVS IPIFLIFSPV  93
X91918   SRGPSTNQIL ALIAGVPIGG  TLITLAGLTL AGSVIGLIVS IPIFLIFSPV  93
Z29859   ---------- ----------  ---------- ---------- ----------
X62352   ---SKSRQIA KAATAVTAGG  SLIVLSSLTL VGTIVIALTVA TPLLVIFSPI  84
Atol3    ---PKARQMV KAATAVTAGG  SLIVISQLTL AGTIVIALTVA TPLLVIFSPV  68
X91956   ESGPSSTQVL SLLIGVPVVG  SLIALAGLLI AGSVIGIMVA LPIFLIFSPV  95
L40954   ESGPSSTQVL SLLIGVPVVG  SLIALAGLLI AGSVIGIMVA LPLFLIFSPV  95

AtS21    IVPAAITIGL AVTGIIASGL  FGLTGLSSVS WVLNYLRGTS DTVPEQLDYA  143
X91918   IVPAAITIGL AVTGIIASGL  FGLTGLSSVS WVLNYLRGTS DTVPEQLDYA  143
Z29859   ---------- ----------  FGLTGLSSVS WVLQLPPWAS DTVPEQVDYA   30
X62352   IVPALITVAL LITGFISSGG  FGIAAITVFS WIYKYATGEH PQGSDKLDSA  134
Atol3    IVPAVVTVAL LITGFIASGG  FGIAAITAFS WLYRHHTGS- --GSDKIENA  115
X91956   IVPAGITIGL AMTGFIASGM  FGLTGLSSIS WVMNYLRGTK RTVPEQLEYA  145
L40954   IVPAAITIGL AMTGFIASGM  FGLTGLSSIS WVMNYLRGTR RTVPEQLEYA  145
```

FIG.7B

```
AtS21    KRRMADAVGY AGMKGKEMGQ YVQDKAHEAR ETEF------ MTETHEPGKA  187
X91918   KRRMADAVGY AGMKGKEMGQ YVQDKAHEAR ETEF------ MTETHEPGKA  187
Z29859   KRRMADAVGY AGMKGKEMGQ YVQDKAHEAR ETEF------ MTETHEPGKA  74
X62352   RMKLGSKA-- QDLKDRA-QY YGQQHTGGEH DRDRTRGGQH TT--------  173
Atol3    RMKVGSRV-- QDTK------ YGQHNIGVQH QQ-------- VS--------  141
X91956   KRRMADAVGY AGQKGKEMGQ HVQNKAQDVK QYDISKPHDT TTKGHETQGG  195
L40954   KRRMADAVGY AGQKGKEMGQ HVQNKAQDVK QYDISKPHDT TTKGHETQGR  195

AtS21    RRGS = Z54164/Atol2    191
X91918   RRGP                   191
Z29859   RRGS                   78
X62352   ----                   173
Atol3    ----                   141
X91956   TTAA                   199
L40954   TTAA                   199
```

FIG.9

```
   1 GAGCTCGATCACACAAGAAAACGTCAAATGGATCATACTGGGCCCATTTGCAGACCAAGAGAAAGTGAGAGAGAGTTG
  81 TCCTCTCGTTATCAGTAAGTAACAGTAGACCACCACCACTAAACCGCCAATAGCTTATAATCAAAATAGAAAGGTCTAATAACAGA
 161 AACAAATGAAAAGCCTTGTTCCATGGACTGCCTACCCGAATTGATTGATTCGACTAGTTTTCTTCTTCTTTGATTAAG
 241 ACCTCCGTAAGAAAAATGTACTACTAAAGCCACTCGCTACCAACTAAAACCATTCCAGACTGTAACTGGACCAATATT
 321 TCTAAACTGTAACCAGATCTCAAACATATAAACTAATTAAGAACTATAAACCGTAAAAATAAATTACTACAGT
 401 AAAAATTATACTAATTTCAGCTATGATGGAATTTCAGCTCTTAAGAGTTGTGGAAATCAAGTAAACCTAAAATCCTAAT
 481 AATATTCTTCATCCTTATTTTGTTTCACATGCTGTCCAATCTGTTATTAGCATTTGAAAGCCTAAAATTCTATAT
 561 ACAGTACAATAAATCTAATTAATTTCATTACTCATATAAAATGCTTCATATATACTCTTGTATTTATAAATCATCCGTTAT
 641 CGTTACTATACCTTTATACATCTACACATTCATCCTACGGCTAGCCAAAGCAACTACTAAAAGGGTCGTCAACGCAAG
 721 TTATTTGCTAGTTGGTGCATACTACACACGCTACGGCAACATTAAGTAACACATTAAGAGGTGTTTTCTTAATGTAGTA
 801 TGGTAATTATATTATTTCAAAACTTGGATTAGATATACAGCTGTGAGAAGAGGGATAAATACAAAAGGAAGATGTTTTGCCGAC
 881 TTAAGCGGATATAGGAGGCATATAAGTACAGCATCGAGAGGAGAGCAATTGTAAAATGGATGATTTGTTGGTTTGTACGGTGGAGAG
 961 AGAGAAAGGTAGATTAAGTAGGCATCGAGAGAGAGCAATTGTAAAATCATGCAAAGCCACACTCTCCCTTCAACACAGTCTTAC
1041 AAGAACGAAAAGATGATCAGTAGAAAATGAAACTTGAAATCATGCAAAGCCAAATATGTCAATCCCATTTATATGTACGTTCTCTT
1121 GTGTCGTCTTCTCTCACTCCATATCTCCTTTTATTACCAAGAAATATGTCAATCCCATTTATATG̲a̲c̲a̲t̲g̲a̲c̲a̲t̲g̲g̲c̲g̲a̲a̲t̲g̲t̲
1201 AGACTTATCTCTATATACCCCCTTTTAATTTGTGTGCTCttag|ccttactctatagtttagata|catggcgaatgt
1281 ggatcgtgatcggctggtgcatgtgcatgtagaccgtcatgtgcatgtagatgatgatgtcggtttg
1361 gtggctatggcggttatggtgctggttctgattataagagtcgcggccctccactaaccaaGTATTTTGTGGTCTCTT
1441 TAGTTTTTCTTGTGTTTTTCCTATGATCACGCTCTCCAAACTATTTGAAGATTTTCTGTAAATTCATTTAAACAGAAAGA
1521 TAAATAAAATAGTGAAGAACCATAGAGAATCGTACGTTACGTTTAATTATTTCCTTTTAGTTCTTAAGTCCTAATTAGGATT
1601 CCTTTAAAAGTTGCAACAATCTAATTGTTCACAAAATGAGTAAAGTTTGAAACAGATTTTTATACACCACTTGCATATGT
1681 TTATCATGGTGATGCATGCTTGTTGTTAGATAAACTCGATATAATCAATACATGCAGatcttggcacttatagcaggagttcc
1761 cattggtggcacactgctaaccctagctgactcactctagccgtttcgtgatcggcttgctagtctccatacccctct
1821 tcctcctttcagtcggtgatatcggcgtcccggctctccactattgggcttgtgacggaatcttggcttctggtttg
1901 tttgggttgacgggtctgagctc
```

FIG.11A  FIG.11B    FIG.11C
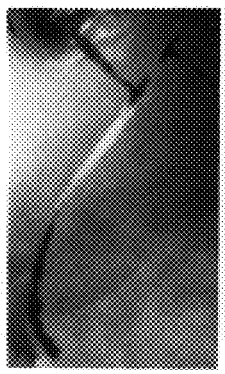  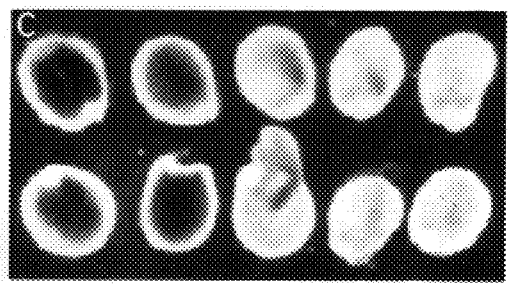
FIG.11D FIG.11E FIG.11F    FIG.11G
   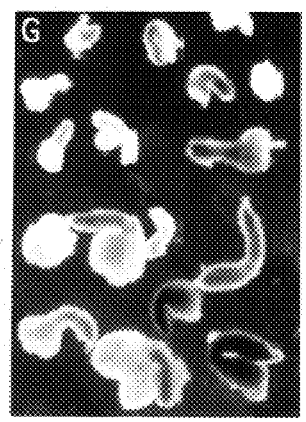
FIG.11H    FIG.11I    FIG.11J
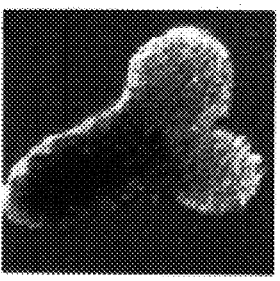 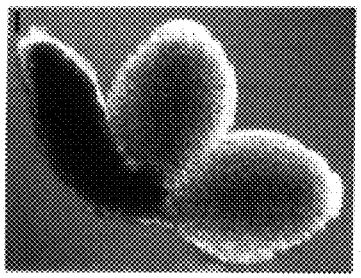 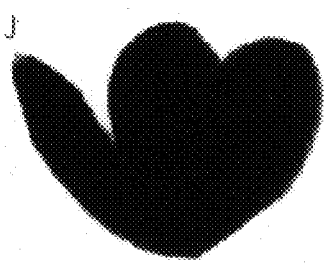
FIG.11K   FIG.11L FIG.11M FIG.11N
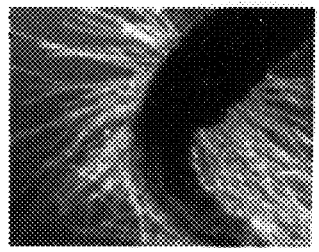 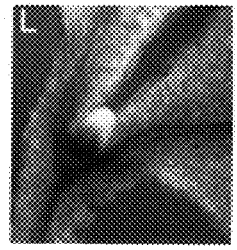  

FIG.12A
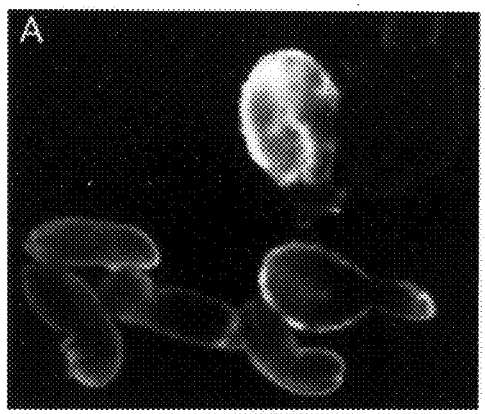
FIG.12B
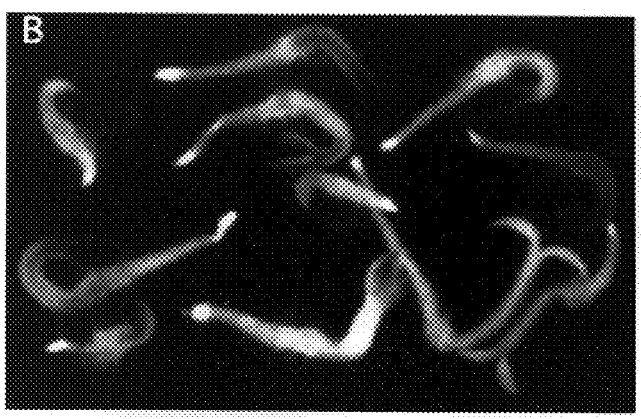
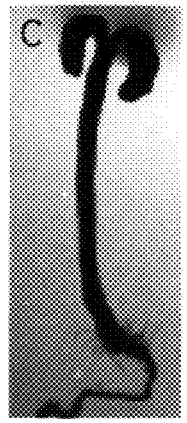
FIG.12C
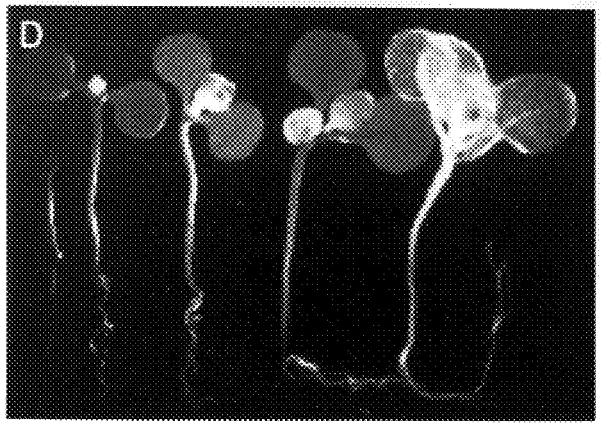
FIG.12D

FIG. 15B
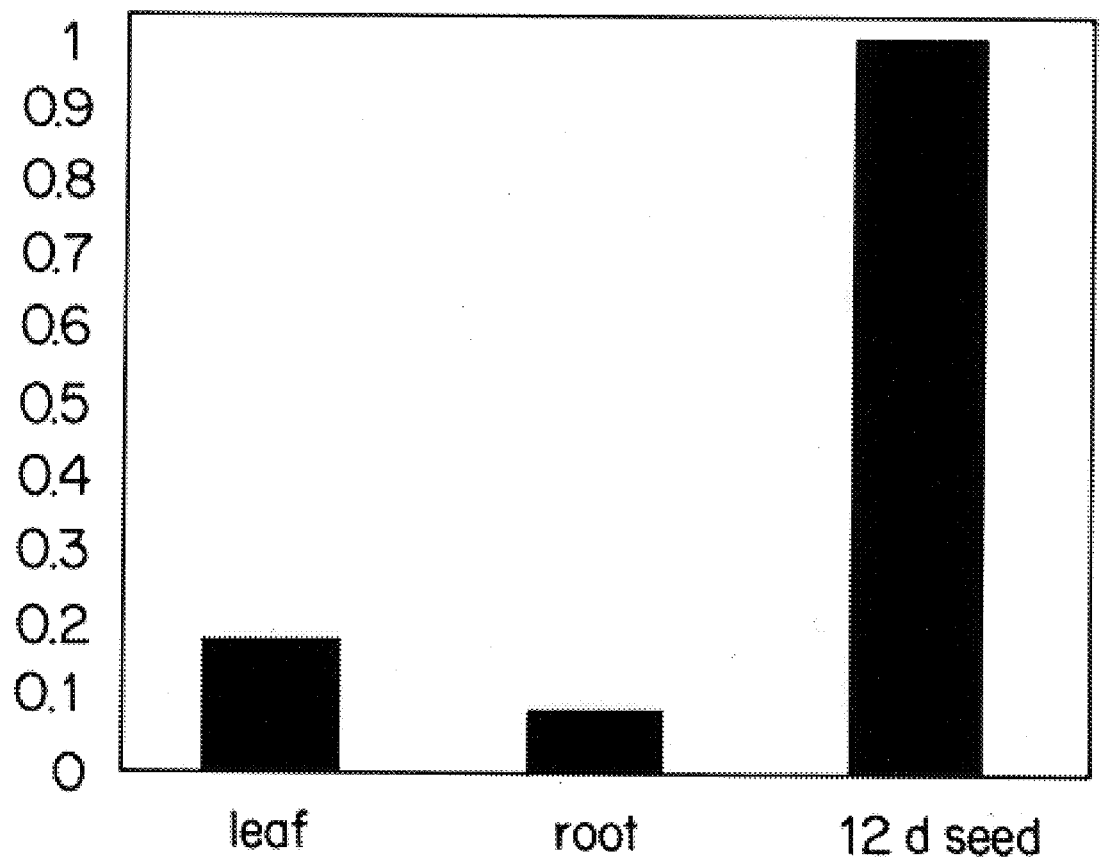
Borage tissue
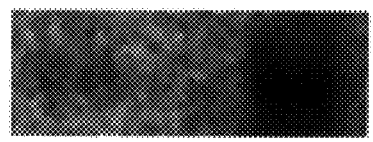
FIG. 15A

OLEOSIN 5' REGULATORY REGION FOR THE MODIFICATION OF PLANT SEED LIPID COMPOSITION

BACKGROUND OF THE INVENTION

Seed oil content has traditionally been modified by plant breeding. The use of recombinant DNA technology to alter seed oil composition can accelerate this process and in some cases alter seed oils in a way that cannot be accomplished by breeding alone. The oil composition of Brassica has been significantly altered by modifying the expression of a number of lipid metabolism genes. Such manipulations of seed oil composition have focused on altering the proportion of endogenous component fatty acids. For example, antisense repression of the Δ12-desaturase gene in transgenic rapeseed has resulted in an increase in oleic acid of up to 83%. Topfer et al. 1995 *Science* 268:681–686.

There have been some successful attempts at modifying the composition of seed oil in transgenic plants by introducing new genes that allow the production of a fatty acid that the host plants were not previously capable of synthesizing. Van de Loo, et al. (1995 *Proc. Natl. Acad. Sci USA* 92:6743–6747) have been able to introduce a Δ12-hydroxylase gene into transgenic tobacco, resulting in the introduction of a novel fatty acid, ricinoleic acid, into its seed oil. The reported accumulation was modest from plants carrying constructs in which transcription of the hydroxylase gene was under the control of the cauliflower mosaic virus (CaMV) 35S promoter. Similarly, tobacco plants have been engineered to produce low levels of petroselinic acid by expression of an acyl-ACP desaturase from coriander (Cahoon et al. 1992 *Proc. Natl. Acad. Sci USA* 89:11184–11188).

The long chain fatty acids (C18 and larger), have significant economic value both as nutritionally and medically important foods and as industrial commodities (Ohlrogge, J. B. 1994 *Plant Physiol.* 104:821–826). Linoleic (18:2 Δ9,12) and α-linolenic acid (18:3 Δ9,12,15) are essential fatty acids found in many seed oils. The levels of these fatty-acids have been manipulated in oil seed crops through breeding and biotechnology (Ohlrogge, et al. 1991 *Biochim. Biophys. Acta* 1082:1–26; Topfer et al. 1995 *Science* 268:681–686). Additionally, the production of novel fatty acids in seed oils can be of considerable use in both human health and industrial applications.

Consumption of plant oils rich in γ-linolenic acid (GLA) (18:3 Δ6,9,12) is thought to alleviate hypercholesterolemia and other related clinical disorders which correlate with susceptibility to coronary heart disease (Brenner R. R. 1976 *Adv. Exp. Med. Biol.* 83:85–101). The therapeutic benefits of dietary GLA may result from its role as a precursor to prostaglandin synthesis (Weete, J. D. 1980 in *Lipid Biochemistry of Fungi and Other Organisms*, eds. Plenum Press, New York, pp. 59–62). Linoleic acid(18:2) (LA) is transformed into gamma linolenic acid (18:3) (GLA) by the enzyme Δ6-desaturase.

Few seed oils contain GLA despite high contents of the precursor linoleic acid. This is due to the absence of Δ6-desaturase activity in most plants. For example, only borage (*Borago officinalis*), evening primrose (*Oenothera biennis*), and currants (*Ribes nigrum*) produce appreciable amounts of linolenic acid. Of these three species, only Oenothera and Borage are cultivated as a commercial source for GLA. It would be beneficial if agronomic seed oils could be engineered to produce GLA in significant quantities by introducing a heterologous Δ6-desaturase gene. It would also be beneficial if other expression products associated with fatty acid synthesis and lipid metabolism could be produced in plants at high enough levels so that commercial production of a particular expression product becomes feasible.

As disclosed in U.S. Pat. No. 5,552,306, a cyanobacterial Δ$^6$-desaturase gene has been recently isolated. Expression of this cyanobacterial gene in transgenic tobacco resulted in significant but low level GLA accumulation. (Reddy et al. 1996 *Nature Biotech.* 14:639–642). Applicant's copending U.S. application Ser. No. 08/366,779, discloses a Δ6-desaturase gene isolated from the plant *Borago officinalis* and its expression in tobacco under the control of the CaMV 35S promoter. Such expression resulted in significant but low level GLA and octadecatetraenoic acid (ODTA or OTA) accumulation in seeds. Thus, a need exists for a promoter which functions in plants and which consistently directs high level expression of lipid metabolism genes in transgenic plant seeds.

Oleosins are abundant seed proteins associated with the phospholipid monolayer membrane of oil bodies. The first oleosin gene, L3, was cloned from maize by selecting clones whose in vitro translated products were recognized by an anti-L3 antibody (Vance et al. 1987 *J. Biol. Chem.* 262:11275–11279). Subsequently, different isoforms of oleosin genes from such different species as Brassica, soybean, carrot, pine, and Arabidopsis have been cloned (Huang, A. H. C., 1992, *Ann. Reviews Plant Phys. and Plant Mol. Biol.* 43:177–200; Kirik et al., 1996 *Plant Mol. Biol.* 31:413–417; Van Rooijen et al., 1992 *Plant Mol. Biol.* 18:1177–1179; Zou et al., *Plant Mol. Biol.* 31:429–433. Oleosin protein sequences predicted from these genes are highly conserved, especially for the central hydrophobic domain. All of these oleosins have the characteristic feature of three distinctive domains. An amphipathic domain of 40–60 amino acids is present at the N-terminus; a totally hydrophobic domain of 68–74 amino acids is located at the center; and an amphipathic α-helical domain of 33–40 amino acids is situated at the C-terminus (Huang, A. H. C. 1992).

The present invention provides 5' regulatory sequences from an oleosin gene which direct high level expression of lipid metabolism genes in transgenic plants. In accordance with the present invention, chimeric constructs comprising an oleosin 5' regulatory region operably linked to coding sequence for a lipid metabolism gene such as a Δ6-desaturase gene are provided. Transgenic plants comprising the subject chimeric constructs produce levels of GLA approaching the level found in those few plant species which naturally produce GLA such as evening primrose (*Oenothera biennis*).

SUMMARY OF THE INVENTION

The present invention is directed to 5' regulatory regions of an Arabidopsis oleosin gene. The 5' regulatory regions, when operably linked to either the coding sequence of a heterologous gene or sequence complementary to a native plant gene, direct expression of the heterologous gene or complementary sequence in a plant seed.

The present invention thus provides expression cassettes and expression vectors comprising an oleosin 5' regulatory region operably linked to a heterologous gene or a sequence complementary to a native plant gene.

Plant transformation vectors comprising the expression cassettes and expression vectors are also provided as are plant cells transformed by these vectors, and plants and their progeny containing the vectors.

In one embodiment of the invention, the heterologous gene or complementary gene sequence is a fatty acid synthesis gene or a lipid metabolism gene.

In another aspect of the present invention, a method is provided for producing a plant with increased levels of a product of a fatty acid synthesis or lipid metabolism gene.

In particular, there is provided a method for producing a plant with increased levels of a fatty acid synthesis or lipid metabolism gene by transforming a plant with the subject expression cassettes and expression vectors which comprise an oleosin 5' regulatory region and a coding sequence for a fatty acid synthesis or lipid metabolism gene.

In another aspect of the present invention, there is provided a method for cosuppressing a native fatty acid synthesis or lipid metabolism gene by transforming a plant with the subject expression cassettes and expression vectors which comprise an oleosin 5' regulatory region and a coding sequence for a fatty acid synthesis or lipid metabolism gene.

A further aspect of this invention provides a method of decreasing production of a native plant gene such as a fatty acid synthesis gene or a lipid metabolism gene by transforming a plant with an expression vector comprising a oleosin 5' regulatory region operably linked to a nucleic acid sequence complementary to a native plant gene.

Also provided are methods of modulating the levels of a heterologous gene such as a fatty acid synthesis or lipid metabolism gene by transforming a plant with the subject expression cassettes and expression vectors.

BRIEF DESCRIPTION OF THE DRAWINGS

FIG. 1 depicts the nucleotide and corresponding amino acid sequence of the borage Δ6-desaturase gene (SEQ ID NO:1). The cytochrome b5 heme-binding motif is boxed and the putative metal binding, histidine rich motifs (HRMs) are underlined.

FIG. 3A provides a gas liquid chromatography profile of the fatty acid methyl esters (FAMES) derived from leaf tissue of a wild type tobacco 'Xanthi'.

FIG. 3B provides a gas liquid chromatography profile of the FAMES derived from leaf tissue of a tobacco plant transformed with the borage Δ6-desaturase cDNA under transcriptional control of the CaMV 35S promoter (pAN2). Peaks corresponding to methyl linoleate (18:2), methyl γ-linolenate (18:3γ), methyl α-linolenate (18:3α), and methyl octadecatetraenoate (18:4) are indicated.

FIG. 4 is the nucleotide sequence and corresponding amino acid sequence of the oleosin AtS21 cDNA (SEQ ID NO:2).

FIG. 7 is a sequence alignment of oleosins isolated from Arabidopsis. Oleosin sequences published or deposited in EMBL, BCM, NCBI databases were aligned to each other using GeneWorks®2.3. Identical residues are boxed with rectangles. The seven sequences fall into three groups. The first group includes AtS21 (SEQ ID NO:3), X91918 (SEQ ID NO:4) and Z29859 (SEQ ID NO:5). The second group includes X62352 (SEQ ID NO:6) and Ato13 (SEQ ID NO:7). The third group includes X91956 (SEQ ID NO:8) and L40954 (SEQ ID NO:9). Differences in amino acid residues within the same group are indicated by shadows. Ato2/Z54164 is identical to AtS21. Ato13 sequence (Accession No. Z541654 in EMBL database) is actually not disclosed in the EMBL database. The Z54165 Accession number designates the same sequence as Z54164 which is Ato12.

FIG. 9 is the nucleotide sequence of the SacI fragment of AtS21 genomic DNA. The promoter and intron sequences are in uppercase. The fragments corresponding to AtS21 cDNA sequence are in lower case. The first ATG codon and a putative TATA box are shadowed. The sequence complementary to 21P primer for PCR amplification is boxed. A putative abscisic acid response element (ABRE) and two 14 bp repeats are underlined.

FIG. 11A depicts AtS21/GUS gene expression in Arabidopsis bolt and leaves.

FIG. 11B depicts AtS21 GUS gene expression in Arabidopsis siliques.

FIG. 11C depicts AtS21 GUS gene expression in Arabidopsis developing seeds.

FIGS. 11D through 11J depict AtS21 GUS gene expression in Arabidopsis developing embryos.

FIG. 11K depicts AtS21/GUS gene expression in Arabidopsis root and root hairs of a young seedling.

FIG. 11L depicts AtS21/GUS gene expression in Arabidopsis cotyledons and the shoot apex of a five day seedling.

FIGS. 11M and 11N depict AtS21/GUS gene expression in Arabidopsis cotyledons and the shoot apex of 5–15 day seedlings.

FIG. 12A depicts AtS21/GUS gene expression in tobacco embryos and endosperm.

FIG. 12B depicts AtS21/GUS gene expression in germinating tobacco seeds.

FIG. 12C depicts AtS21/GUS gene expression in a 5 day old tobacco seedling.

FIG. 12D depicts AtS21/GUS gene expression in 5–15 day old tobacco seedlings.

FIG. 15A is an RNA gel blot analysis carried out on 5 μg samples of RNA isolated from borage leaf, root, and 12 dpp embryo tissue, using labeled borage Δ6-desaturase cDNA as a hybridization probe.

FIG. 15B depicts a graph corresponding to the Northern analysis results for the experiment shown in FIG. 15A.

DETAILED DESCRIPTION OF THE INVENTION

Figure 2:
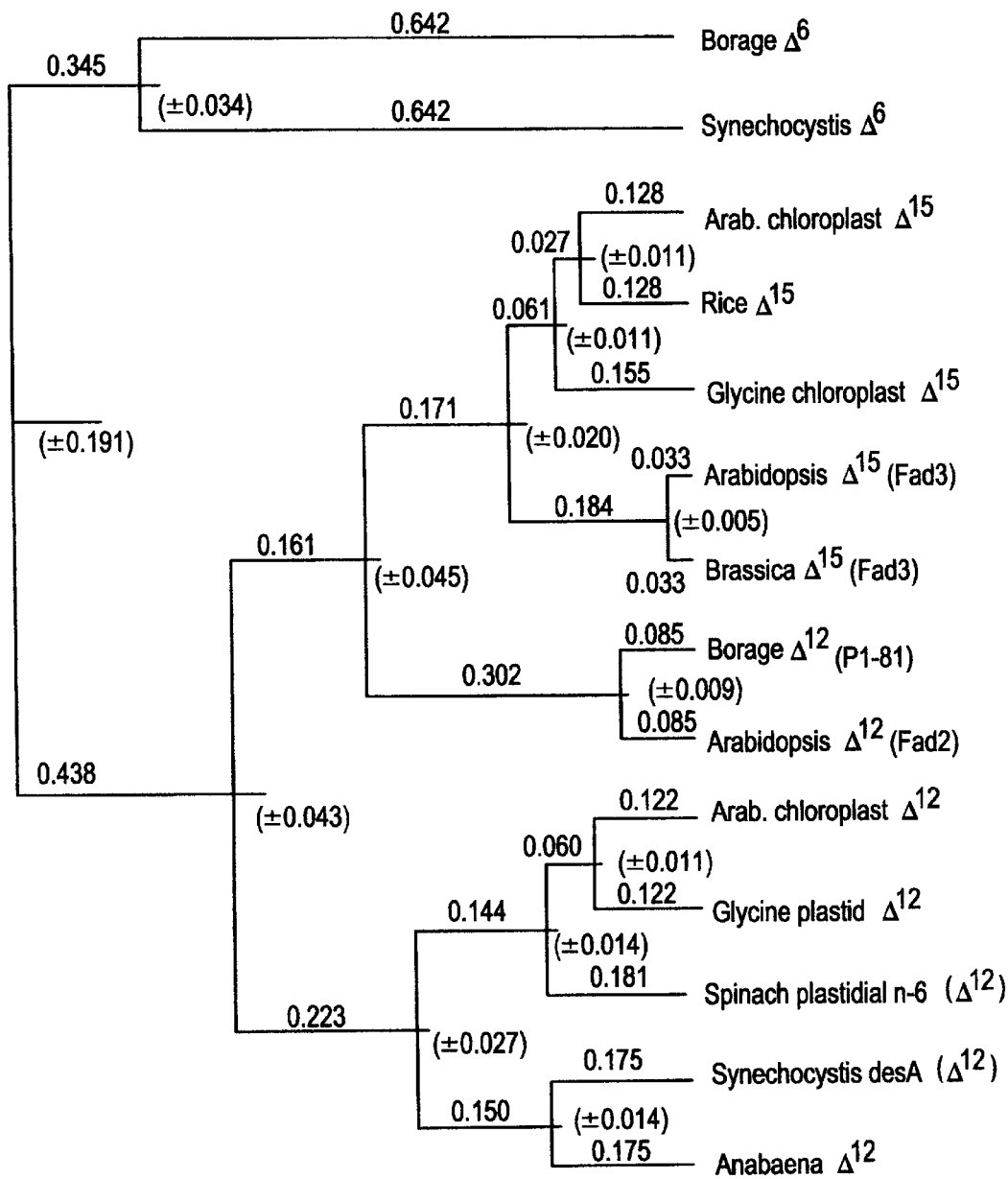
FIG. 2 is a dendrogram showing similarity of the borage Δ6-desaturase to other membrane-bound desaturases. The amino acid sequence of the borage Δ6-desaturase was compared to other known desaturases using Gene Works (IntelliGenetics). Numerical values correlate to relative phylogenetic distances between subgroups compared.

The present invention provides isolated nucleic acids encoding 5' regulatory regions from an Arabidopsis oleosin gene. In accordance with the present invention, the subject 5' regulatory regions, when operably linked to either a coding sequence of a heterologous gene or a sequence complementary to a native plant gene, direct expression of the coding sequence or complementary sequence in a plant seed. The oleosin 5' regulatory regions of the present invention are useful in the construction of an expression cassette which comprises in the 5' to 3' direction, a subject oleosin 5' regulatory region, a heterologous gene or sequence complementary to a native plant gene under control of the regulatory region and a 3' termination sequence. Such an expression cassette can be incorporated into a variety of autonomously replicating vectors in order to construct an expression vector.

It has been surprisingly found that plants transformed with the expression vectors of the present invention produce levels of GLA approaching the level found in those few plant species which naturally produce GLA such as evening primrose (*Oenothera biennis*).

As used herein, the term "cassette" refers to a nucleotide sequence capable of expressing a particular gene if said gene is inserted so as to be operably linked to one or more regulatory regions present in the nucleotide sequence. Thus, for example, the expression cassette may comprise a heterologous coding sequence which is desired to be expressed in a plant seed. The expression cassettes and expression vectors of the present invention are therefore useful for directing seed-specific expression of any number of heterologous genes. The term "seed-specific expression" as used herein, refers to expression in various portions of a plant seed such as the endosperm and embryo.

An isolated nucleic acid encoding a 5' regulatory region from an oleosin gene can be provided as follows. Oleosin recombinant genomic clones are isolated by screening a plant genomic DNA library with a cDNA (or a portion thereof) representing oleosin mRNA. A number of different oleosin cDNAs have been isolated. The methods used to isolate such cDNAs as well as the nucleotide and corresponding amino acid sequences have been published in Kirik et al. 1986 *Plant Mol. Biol.* 31:413–417; Zou et al. *Plant Mol. Biol.* 31:429–433; Van Rooigen et al. 1992 *Plant Mol. Biol.* 18:1177–1179.

Virtual subtraction screening of a tissue specific library using a random primed polymerase chain (RP-PCR) cDNA probe is another method of obtaining an oleosin cDNA useful for screening a plant genomic DNA library. Virtual subtraction screening refers to a method where a cDNA library is constructed from a target tissue and displayed at a low density so that individual cDNA clones can be easily separated. These cDNA clones are subtractively screened with driver quantities (i.e., concentrations of DNA to kinetically drive the hybridization reaction) of cDNA probes made from tissue or tissues other than the target tissue (i.e. driver tissue). The hybridized plaques represent genes that are expressed in both the target and the driver tissues; the unhybridized plaques represent genes that may be target tissue-specific or low abundant genes that can not be detected by the driver cDNA probe. The unhybridized cDNAs are selected as putative target tissue-specific genes and further analyzed by one-pass sequencing and Northern hybridization.

Random primed PCR (RP-PCR) involves synthesis of large quantities of cDNA probes from a trace amount of cDNA template. The method combines the amplification power of PCR with the representation of random priming to simultaneously amplify and label double-stranded cDNA in a single tube reaction.

Methods considered useful in obtaining oleosin genomic recombinant DNA are provided in Sambrook et al. 1989, in *Molecular Cloning: A Laboratory Manual*, Cold Spring Harbor, N.Y., for example, or any of the myriad of laboratory manuals on recombinant DNA technology that are widely available. To determine nucleotide sequences, a multitude of techniques are available and known to the ordinarily skilled artisan. For example, restriction fragments containing an oleosin regulatory region can be subcloned into the polylinker site of a sequencing vector such as pBluescript (Stratagene). These pBluescript subclones can then be sequenced by the double-stranded dideoxy method (Chen and Seeburg, 1985, *DNA* 4:165).

In a preferred embodiment, the oleosin regulatory region comprises nucleotides 1–1267 of FIG. 9 (SEQ ID NO:10). Modifications to the oleosin regulatory region as set forth in SEQ ID NO:10 which maintain the characteristic property of directing seed-specific expression, are within the scope of the present invention. Such modifications include insertions, deletions and substitutions of one or more nucleotides.

The 5' regulatory region of the present invention can be derived from restriction endonuclease or exonuclease digestion of an oleosin genomic clone. Thus, for example, the known nucleotide or amino acid sequence of the coding region of an isolated oleosin gene (e.g. FIG. 7) is aligned to the nucleic acid or deduced amino acid sequence of an isolated oleosin genomic clone and 5' flanking sequence (i.e., sequence upstream from the translational start codon of the coding region) of the isolated oleosin genomic clone located.

The oleosin 5' regulatory region as set forth in SEQ ID NO:10 (nucleotides 1–1267 of FIG. 9) may be generated from a genomic clone having either or both excess 5' flanking sequence or coding sequence by exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base" system. Alternatively, PCR primers can be defined to allow direct amplification of the subject 5' regulatory regions.

Using the same methodologies, the ordinarily skilled artisan can generate one or more deletion fragments of nucleotides 1–1267 as set forth in SEQ ID NO:10. Any and all deletion fragments which comprise a contiguous portion of nucleotides set forth in SEQ ID NO:10 and which retain the capacity to direct seed-specific expression are contemplated by the present invention.

The identification of oleosin 5' regulatory sequences which direct seed-specific expression comprising nucleotides 1–1267 of SEQ ID NO:10 and modifications or deletion fragments thereof, can be accomplished by transcriptional fusions of specific sequences with the coding sequences of a heterologous gene, transfer of the chimeric gene into an appropriate host, and detection of the expression of the heterologous gene. The assay used to detect expression depends upon the nature of the heterologous sequence. For example, reporter genes, exemplified by chloramphenicol acetyl transferase and β-glucuronidase (GUS), are commonly used to assess transcriptional and translational competence of chimeric constructions. Standard assays are available to sensitively detect the reporter enzyme in a transgenic organism. The β-glucuronidase (GUS) gene is useful as a reporter of promoter activity in transgenic plants because of the high stability of the enzyme in plant cells, the lack of intrinsic β-glucuronidase activity in higher plants and availability of a quantitative fluorimetric assay and a histochemical localization technique. Jerfferson et al. (1987 *EMBO J* 6:3901) have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methylumbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such chimeric genes allows definition of specific regulatory sequences and demonstrates that these sequences can direct expression of heterologous genes in a seed-specific manner.

Another aspect of the invention is directed to expression cassettes and expression vectors (also termed herein "chimeric genes") comprising a 5' regulatory region from an oleosin gene which directs seed specific expression operably linked to the coding sequence of a heterologous gene such that the regulatory element is capable of controlling expression of the product encoded by the heterologous gene. The heterologous gene can be any gene other than oleosin. If necessary, additional regulatory elements or parts of these elements sufficient to cause expression resulting in production of an effective amount of the polypeptide encoded by the heterologous gene are included in the chimeric constructs.

Accordingly, the present invention provides chimeric genes comprising sequences of the oleosin 5' regulatory region that confer seed-specific expression which are operably linked to a sequence encoding a heterologous gene such as a lipid metabolism enzyme. Examples of lipid metabolism genes useful for practicing the present invention include lipid desaturases such as Δ6-desaturases, Δ12-desaturases, Δ15-desaturases and other related desaturases such as stearoyl-ACP desaturases, acyl carrier proteins (ACPs), thioesterases, acetyl transacylases, acetyl-coA carboxylases, ketoacyl-synthases, malonyl transacylases, and elongases. Such lipid metabolism genes have been isolated and characterized from a number of different bacteria and plant species. Their nucleotide coding sequences as well as methods of isolating such coding sequences are disclosed in the published literature and are widely available to those of skill in the art.

In particular, the Δ6-desaturase genes disclosed in U.S. Pat. No. 5,552,306 and applicants' copending U.S. application Ser. No. 08/366,779 filed Dec. 30, 1994 now U.S. Pat. No. 5,614,393, and incorporated herein by reference, are contemplated as lipid metabolism genes particularly useful in the practice of the present invention.

The chimeric genes of the present invention are constructed by ligating a 5' regulatory region of a oleosin genomic DNA to the coding sequence of a heterologous gene. The juxtaposition of these sequences can be accomplished in a variety of ways. In a preferred embodiment the order of the sequences, from 5' to 3', is an oleosin 5' regulatory region (including a promoter), a coding sequence, and a termination sequence which includes a polyadenylation site.

Standard techniques for construction of such chimeric genes are well known to those of ordinary skill in the art and can be found in references such as Sambrook et al.(1989). A variety of strategies are available for ligating fragments of DNA, the choice of which depends on the nature of the termini of the DNA fragments. One of ordinary skill in the art recognizes that in order for the heterologous gene to be expressed, the construction requires promoter elements and signals for efficient polyadenylation of the transcript. Accordingly, the oleosin 5' regulatory region that contains the consensus promoter sequence known as the TATA box can be ligated directly to a promoterless heterologous coding sequence.

The restriction or deletion fragments that contain the oleosin TATA box are ligated in a forward orientation to a promoterless heterologous gene such as the coding sequence of β-glucuronidase (GUS). The skilled artisan will recognize that the subject oleosin 5' regulatory regions can be provided by other means, for example chemical or enzymatic synthesis. The 3' end of a heterologous coding sequence is optionally ligated to a termination sequence comprising a polyadenylation site, exemplified by, but not limited to, the nopaline synthase polyadenylation site, or the octopine T-DNA gene 7 polyadenylation site. Alternatively, the polyadenylation site can be provided by the heterologous gene.

The present invention also provides methods of increasing levels of heterologous genes in plant seeds. In accordance with such methods, the subject expression cassettes and expression vectors are introduced into a plant in order to effect expression of a heterologous gene. For example, a method of producing a plant with increased levels of a product of a fatty acid synthesis or lipid metabolism gene is provided by transforming a plant cell with an expression vector comprising an oleosin 5' regulatory region operably linked to a fatty acid synthesis or lipid metabolism gene and regenerating a plant with increased levels of the product of said fatty acid synthesis or lipid metabolism gene.

Another aspect of the present invention provides methods of reducing levels of a product of a gene which is native to a plant which comprises transforming a plant cell with an expression vector comprising a subject oleosin regulatory region operably linked to a nucleic acid sequence which is complementary to the native plant gene. In this manner, levels of endogenous product of the native plant gene are reduced through the mechanism known as antisense regulation. Thus, for example, levels of a product of a fatty acid synthesis gene or lipid metabolism gene are reduced by transforming a plant with an expression vector comprising a subject oleosin 5' regulatory region operably linked to a nucleic acid sequence which is complementary to a nucleic acid sequence coding for a native fatty acid synthesis or lipid metabolism gene.

The present invention also provides a method of cosuppressing a gene which is native to a plant which comprises transforming a plant cell with an expression vector comprising a subject oleosin 5' regulatory region operably linked to a nucleic acid sequence coding for the native plant gene. In this manner, levels of endogenous product of the native plant gene are reduced through the mechanism known as cosuppression. Thus, for example, levels of a product of a fatty acid synthesis gene or lipid metabolism gene are reduced by transforming a plant with an expression vector comprising a subject oleosin 5' regulatory region operably linked to a nucleic acid sequence coding for a native fatty acid synthesis or lipid metabolism gene native to the plant. Although the exact mechanism of cosuppression is not completely understood, one skilled in the art is familiar with published works reporting the experimental conditions and results associated with cosuppression (Napoli et al. 1990 *The Plant Cell* 2:270–289; Van der Krol 1990 *The Plant Cell* 2:291–299.

To provide regulated expression of the heterologous or native genes, plants are transformed with the chimeric gene constructions of the invention. Methods of gene transfer are well known in the art. The chimeric genes can be introduced into plants by leaf disk transformation-regeneration procedure as described by Horsch et al. 1985 *Science* 227:1229. Other methods of transformation such as protoplast culture (Horsch et al. 1984 *Science* 223:496, DeBlock et al. 1984 *EMBO J.* 2:2143, Barton et al. 1983, *Cell* 32:1033) can also be used and are within the scope of this invention. In a preferred embodiment, plants are transformed with Agrobacterium-derived vectors such as those described in Klett et al. (1987) *Annu. Rev. Plant Physiol.* 38:467. Other well-known methods are available to insert the chimeric genes of the present invention into plant cells. Such alternative methods include biolistic approaches (Klein et al. 1987 *Nature* 327:70), electroporation, chemically-induced DNA uptake, and use of viruses or pollen as vectors.

When necessary for the transformation method, the chimeric genes of the present invention can be inserted into a plant transformation vector, e.g. the binary vector described by Bevan, M. 1984 *Nucleic Acids Res.* 12:8711–8721. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Surface-sterilized leaf disks and other susceptible tissues are inoculated with the "disarmed" foreign DNA-containing *A. tumefaciens*, cultured for a number of days, and then transferred to antibiotic-containing medium. Transformed shoots are then selected after rooting in medium containing the appropriate antibiotic, and transferred to soil. Transgenic plants are pollinated and seeds from these plants are collected and grown on antibiotic medium.

Expression of a heterologous or reporter gene in developing seeds, young seedlings and mature plants can be monitored by immunological, histochemical or activity assays. As discussed herein, the choice of an assay for expression of the chimeric gene depends upon the nature of the heterologous coding region. For example, Northern analysis can be used to assess transcription if appropriate nucleotide probes are available. If antibodies to the polypeptide encoded by the heterologous gene are available, Western analysis and immunohistochemical localization can be used to assess the production and localization of the polypeptide. Depending upon the heterologous gene, appropriate biochemical assays can be used. For example, acetyltransferases are detected by measuring acetylation of a standard substrate. The expression of a lipid desaturase gene can be assayed by analysis of fatty acid methyl esters (FAMES).

Another aspect of the present invention provides transgenic plants or progeny of these plants containing the chimeric genes of the invention. Both monocotyledonous and dicotyledonous plants are contemplated. Plant cells are transformed with the chimeric genes by any of the plant transformation methods described above. The transformed plant cell, usually in the form of a callus culture, leaf disk, explant or whole plant (via the vacuum infiltration method of Bechtold et al. 1993 *C.R. Acad. Sci. Paris*, 316:1194–1199) is regenerated into a complete transgenic plant by methods well-known to one of ordinary skill in the art (e.g. Horsh et al. 1985 *Science* 227:1129). In a preferred embodiment, the transgenic plant is sunflower, cotton, oil seed rape, maize, tobacco, Arabidopsis, peanut or soybean. Since progeny of transformed plants inherit the chimeric genes, seeds or cuttings from transformed plants are used to maintain the transgenic line.

The following examples further illustrate the invention.

EXAMPLE 1

Isolation of Membrane-Bound Polysomal RNA and Construction of Borage cDNA Library Membrane-bound polysomes were isolated from borage seeds 12 days post pollination (12 DPP) using the protocol established for peas by Larkins and Davies (1975 *Plant Phys.* 55: 749–756). RNA was extracted from the polysomes as described by Mechler (1987 *Methods in Enzymology* 152: 241–248, Academic Press). Poly-A$^+$ RNA was isolated from the membrane bound polysomal RNA using Oligotex-dT™ beads (Qiagen).

Corresponding cDNA was made using Stratagene's ZAP cDNA synthesis kit. The cDNA library was constructed in the lambda ZAP II vector (Stratagene) using the lambda ZAP II kit. The primary library was packaged with Gigapack II Gold packaging extract (Stratagene).

EXAMPLE 2

Isolation of a Δ-6 Desaturase cDNA from Borage
Hybridization protocol

The amplified borage cDNA library was plated at low density (500 pfu on 150 mm petri dishes). Highly prevalent seed storage protein cDNAs were reduced (subtracted from the total cDNAs) by screening with the corresponding cDNAs.

Hybridization probes for screening the borage cDNA library were generated by using random primed DNA synthesis as described by Ausubel et al (1994 *Current Protocols in Molecular Biology*, Wiley Interscience, N.Y.) and corresponded to previously identified abundantly expressed seed storage protein cDNAs. Unincorporated nucleotides were removed by use of a G-50 spin column (Boehringer Manheim). Probe was denatured for hybridization by boiling in a water bath for 5 minutes, then quickly cooled on ice. Nitrocellulose filters carrying fixed recombinant bacteriophage were prehybridized at 60° C. for 2–4 hours in hybridization solution [4X SET (600 mM NaCl, 80 mM Tris-HCl, 4 mM $Na_2EDTA$; pH 7.8), 5X Denhardt's reagent (0.1% bovine serum albumin, 0.1% Ficoll, and 0.1% polyvinylpyrolidone), 100 µg/ml denatured salmon sperm DNA, 50 µg/ml polyadenine and 10 µg/ml polycytidine]. This was replaced with fresh hybridization solution to which denatured radioactive probe (2 ng/ml hybridization solution) was added. The filters were incubated at 60° C. with agitation overnight. Filters were washed sequentially in 4X, 2X, and 1X SET (150 mM NaCl, 20 mM Tris-HCl, 1 mM $Na_2EDTA$; pH7.8) for 15 minutes each at 60° C. Filters were air dried and then exposed to X-ray film for 24 hours with intensifying screens at −80° C.

Non-hybridizing plaques were excised using Stratagene's excision protocol and reagents. Resulting bacterial colonies were used to inoculate liquid cultures and were either sequenced manually or by an ABI automated sequencer.
Random Sequencing of cDNAs from a Borage Seed 12 (DPP) Membrane-Bound Polysomal Library Each cDNA corresponding to a non-hybridizing plaque was sequenced once and a sequence tag generated from 200–300 base pairs. All sequencing was performed by cycle sequencing (Epicentre). Over 300 expressed sequence tags (ESTs) were generated. Each sequence tag was compared to the GenBank database using the BLAST algorithm (Altschul et al. 1990 *J. Mol. Biol.* 215:403–410). A number of lipid metabolism genes, including the Δ6-desaturase were identified.

Database searches with the cDNA clone designated mbp-65 using BLASTX with the GenBank database resulted in a significant match to the previously isolated Synechocystis Δ6-desaturase. It was determined however, that mbp-65 was not a full length cDNA. A full length cDNA was isolated using mbp-65 to screen the borage membrane-bound polysomal library. The resultant clone was designated pAN1 and the cDNA insert of pAN1 was sequenced by the cycle sequencing method. The amino acid sequence deduced from the open reading frame (FIG. 1, SEQ ID NO:1) was compared to other known desaturases using Geneworks (IntelligGenetics) protein alignment program. This alignment indicated that the cDNA insert of pAN1 was the borage Δ6-desaturase gene.

The resulting dendrogram (FIG. 2) shows that $Δ^{15}$-desaturases and $Δ^{12}$-desaturases comprise two groups. The newly isolated borage sequence and the previously isolated Synechocystis Δ6-desaturase (U.S. Pat. No. 5,552,306) formed a third distinct group. A comparison of amino acid motifs common to desaturases and thought to be involved catalytically in metal binding illustrates the overall similarity of the protein encoded by the borage gene to desaturases in general and the Synechocystis $Δ^6$-desaturase in particular (Table 1). At the same time, comparison of the motifs in Table 1 indicates definite differences between this protein and other plant desaturases. Furthermore, the borage sequence is also distinguished from known plant membrane associated fatty acid desaturases by the presence of a heme binding motif conserved in cytochrome $b_5$ proteins (Schmidt et al. 1994 *Plant Mol. Biol.* 26:631–642)(FIG. 1). Thus, while these results clearly suggested that the isolated cDNA was a borage $Δ^6$-desaturase gene, further confirmation was necessary. To confirm the identity of the borage Δ6-desaturase cDNA, the cDNA insert from pAN1 was cloned into an expression cassette for stable expression. The vector pBI121 (Jefferson et al. 1987 *EMBO J.* 6:3901–3907) was prepared for ligation by digestion with BamHI and EcoICRI (an isoschizomer of SacI which leaves blunt ends; available from Promega) which excises the GUS coding region leaving the 35S promoter and NOS terminator intact. The borage $Δ^6$-desaturase cDNA was excised from the recombinant plasmid (pAN1) digestion with BamHI and XhoI. The XhoI end was made blunt by performing a fill-in reaction catalyzed by the Klenow fragment of DNA polymerase I. This fragment was then cloned into the BamHI/EcoICR I sites of pBI121.1, resulting in the plasmid pAN2.

EXAMPLE 3

Production of Transgenic Plants and Preparation and Analysis of Fatty Acid Methyl Esters (FAMEs)

The expression plasmid, pAN2 was used to transform tobacco (*Nicotiana tabacum cv. xanthi*) via *Agrobacterium tumefaciens* according to standard procedures (Horsch, et al. 1985 *Science* 227:1229–1231; Bogue et al. 1990 *Mol. Gen. Genet.* 221:49–57) except that the initial transformants were selected on 100 µg/ml kanamycin.

Tissue from transgenic plants was frozen in liquid nitrogen and lyophilized overnight. FAMEs were prepared as described by Dahmer, et al. (1989) *J. Amer. Oil. Chem. Soc.* 66: 543–548. In some cases, the solvent was evaporated again, and the FAMEs were resuspended in ethyl acetate and extracted once with deionized water to remove any water soluble contaminants. FAMEs were analyzed using a Tracor-560 gas liquid chromatograph as previously described (Reddy et al. 1996 *Nature Biotech.* 14:639–642).

As shown in FIG. 3, transgenic tobacco leaves containing the borage cDNA produced both GLA and octadecatetraenoic acid (OTA) (18:4 Δ6,9,12,15). These results thus demonstrate that the isolated cDNA encodes a borage Δ6-desaturase.

EXAMPLE 4

Expression of Δ6-desaturase in Borage

Figure 16A:
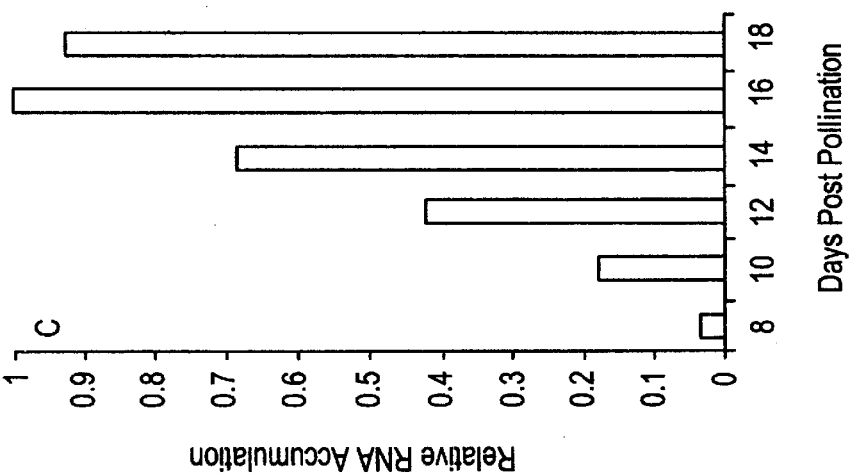
FIG. 16A is a graph showing relative legumin RNA accumulation in developing borage embryos based on results of Northern blot.
Figure 16B:
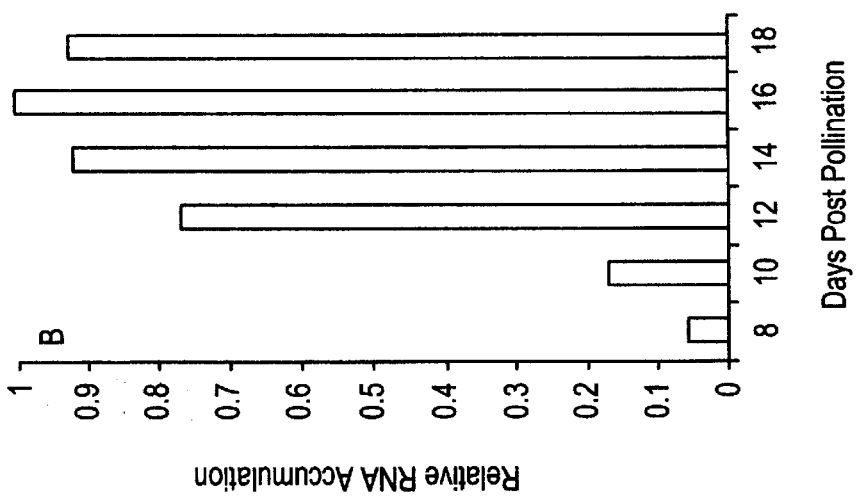
FIG. 16B is a graph showing relative oleosin RNA accumulation in developing borage embryos based on results of Northern blot.
Figure 16C:
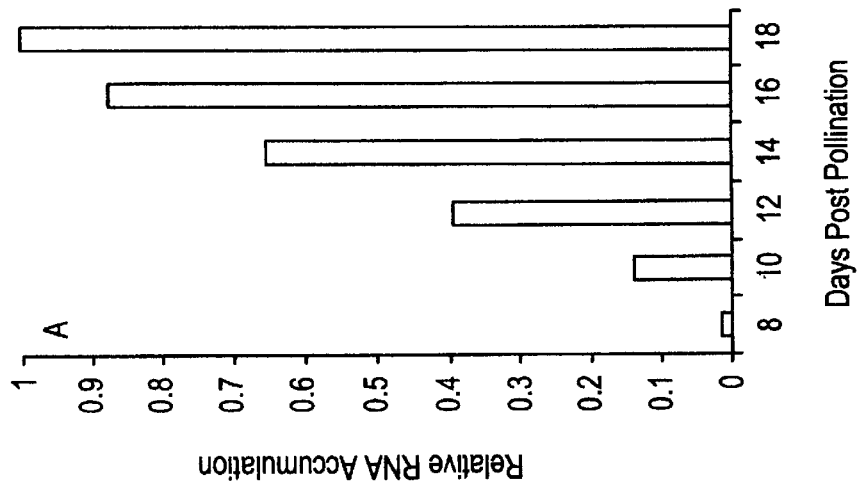
FIG. 16C is a graph showing relative Δ6-desaturase RNA accumulation in developing borage embryos based on results of Northern blot.

The native expression of Δ6-desaturase was examined by Northern Analysis of RNA derived from borage tissues. RNA was isolated from developing borage embryos following the method of Chang et al. 1993 *Plant Mol. Biol. Rep.* 11:113–116. RNA was electrophoretically separated on formaldehyde-agarose gels, blotted to nylon membranes by capillary transfer, and immobilized by baking at 80° C. for 30 minutes following standard protocols (Brown T., 1996 in *Current Protocols in Molecular Biology*, eds. Auselbel, et al. [Greene Publishing and Wiley-Interscience, New York] pp. 4.9.1–4.9.14.). The filters were preincubated at 42° C. in a solution containing 50% deionized formamide, 5X Denhardt's reagent, 5X SSPE (900 mM NaCl; 50 mM Sodium phosphate, pH7.7; and 5 mM EDTA), 0.1% SDS, and 200 µg/ml denatured salmon sperm DNA. After two hours, the filters were added to a fresh solution of the same composition with the addition of denatured radioactive hybridization probe. In this instance, the probes used were borage legumin cDNA (FIG. 16A), borage oleosin cDNA (FIG. 16B), and borage Δ6-desaturase cDNA (pAN1, Example 2)(FIG. 16C). The borage legumin and oleosin cDNAs were isolated by EST cloning and identified by comparison to the GenBank database using the BLAST algorithm as described in Example 2. Loading variation was corrected by normalizing to levels of borage EF1α mRNA. EF1α mRNA was identified by correlating to the corresponding cDNA obtained by the EST analysis described in Example 2. The filters were hybridized at 42° C. for 12–20 hours, then washed as described above (except that the temperature was 65° C.), air dried, and exposed to X-ray film.

As depicted in FIGS. 15A and 15B, Δ6-desaturase is expressed primarily in borage seed. Borage seeds reach maturation between 18–20 days post pollination (dpp). Δ6-desaturase mRNA expression occurs throughout the time points collected (8–20 dpp), but appears maximal from 10–16 days post pollination. This expression profile is similar to that seen for borage oleosin and 12S seed storage protein mRNAs (FIGS. 16A, 16B, and 16C).

EXAMPLE 5

Isolation and Characterization of a Novel Oleosin cDNA

The oleosin cDNA (AtS21) was isolated by virtual subtraction screening of an Arabidopsis developing seed cDNA library using a random primed polymerase chain reaction (RP-PCR) cDNA probe derived from root tissue.

RNA PREPARATION

*Arabidopsis thaliana* Landsberg *erecta* plants were grown under continuous illumination in a vermiculite/soil mixture at ambient temperature (22° C). Siliques 2–5 days after flowering were dissected to separately collect developing seeds and silique coats. Inflorescences containing initial flower buds and fully opened flowers, leaves, and whole siliques one or three days after flowering were also collected. Roots were obtained from seedlings that had been grown in Gamborg $B_5$ liquid medium (GIBCO BRL) for two weeks. The seeds for root culture were previously sterilized with 50% bleach for five minutes and rinsed with water extensively. All tissues were frozen in liquid nitrogen and stored at −80° C. until use. Total RNAs were isolated following a hot phenol/SDS extraction and LiCl precipitation protocol (Harris et al. 1978 *Biochem*. 17:3251–3256; Galau et al. 1981 *J. Biol. Chem*. 256:2551–2560). Poly A+ RNA was isolated using oligo dT column chromatography according to manufacturers' protocols (PHARMACIA or STRATAGENE) or using oligotex-dT latex particles (QIAGEN).

Construction of tissue-specific cDNA libraries

Flower, one day silique, three day silique, leaf, root, and developing seed cDNA libraries were each constructed from 5 µg poly A+ RN using the ZAP cDNA synthesis kit (Stratagene). cDNAs were directionally cloned into the EcoRI and XhoI sites of pBluescript SK(−) in the λ-ZAPII vector (Short et al. 1988 *Nucleic Acids Res.* 16:7583–7600). Nonrecombinant phage plaques were identified by blue color development on NZY plates containing X-gal (5 bromo-4-chloro-3-indoyl-β-D-galactopyranoside) and IPTG (isopropyl-1-thio-β-D-galactopyranoside). The nonrecombinant backgrounds for the flower, one day silique, three day silique, leaf, root, and developing seed cDNA libraries were 2.8%, 2% m 3.3%, 6.5%, 2.5%, and 1.9% respectively.

Random priming DNA labeling

The cDNA inserts of isolated clones (unhybridized cDNAs) were excised by EcoRI/XhoI double digestion and gel-purified for random priming labeling. Klenow reaction mixture contained 50 ng DNA templates, 10 mM Tris-HCl, pH 7.5, 5 mM $MgCl_2$, 7.5 mM DTT, 50 uM each of dCTP, dGTP, and dTTP, 10 uM hexamer random primbers (Boehringer Mannheim), 50 µCi α-32 P-dATP, 3000 Ci/mmole, 10 mCi/ml (DuPont), and 5 units of DNA polymerase I Klenow fragment (New England Biolabs). The reactions were carried out at 37° C. for one hour. Aliquots of diluted reaction mixtures were used for TCA precipitation and alkaline denaturing gel analysis. Hybridization probes were labeled only with Klenow DNA polymerase and the unincorporated dNTPs were removed using Sephadex R G-50 spin columns (Boehringer Mannheim).

Random Primed PCR

Double-stranded cDNA was synthesized from poly A+ RNA isolated from Arabidopsis root tissue using the cDNA Synthesis System (GIBCO BRL) with oligo dT12–18 as primers. cDNAs longer than 300 bp were enriched by Sephacryl S-400 column chromatography (Stratagene). Fractionated cDNAs were used as templates for RP-PCR labeling. The reaction contained 10 mM Tris-HCl, ph 9.0, 50 mM KCl, 0.1% Triton X-100, 2 mM MgCl2, 5 units Taq DNA polymeras (PROMEGA), 200 µM dCTP, cGTP, and dTTP, and different concentrations of hexamer random primers α-32P dATP, 800 mCi/mmole, 10 mCi/ml (DuPont), and cold dATP in a final volume of 25 µl. After an initial 5 minutes at 95° C., different reactions were run through different programs to optimize RP-PCR cDNA conditions. Unless otherwise indicated, the following program was used for most RP-PCR cDNA probe labeling: 95° C./5 minutes, then 40 cycles of 95° C. 30 seconds, 18° C./1 second, ramp to 30° C. at a rate of 0.1° C./second. 72° C./1 minute. RP-PCR products were phenol/chloroform extracted and ethanol precipitated or purified by passing through Sephadex G-50 spin columns (Boehringer Mannheim).

Clone blot virtual subtraction

Mass excision of λ-ZAP cDNA libraries was carried out by co-infecting XL1-Blue MRF' host cells with recombinant phage from the libraries and ExAssist helper phage (STRATAGENE). Excised phagemids were rescued by SOLR cells. Plasmid DNAs were prepared by boiling miniprep method (Holmes et al. 1981 *Anal. Biochem.* 114:193–197) from randomly isolated clones. cDNA inserts were excised by EcoRI and XhoI double digestion, and resolved on 1% agarose gels. The DNAs were denatured in 0.5 N NaOH and 1.5 m NaCl for 45 minutes, neutralized in 0.5 M Tris-HCl, pH 8.0, and 1.5 M NaCl for 45 minutes, and then transferred by blotting to nylon membranes (Micron Separations, Inc.) in 10X SSC overnight. After one hour prehybridization at 65° C., root RP-cDNA probe was added to the same hybridization buffer containing 1% bovine albumin fraction V (Sigma), 1 mM EDTA, 0.5 M NaHPO4, pH 7.2, 7% SDS. The hybridization continued for 24 hours at 65° C. The filters were washed in 0.5% bovine albumin, 1 mM EDTA, 40 mM NaHPO4, pH 7.2, 5% SDS for ten minutes at room temperature, and 3×10 minutes in 1 mM EDTA, 40 mM NaHPO4, pH 7.2, 1% SDS at 65° C. Autoradiographs were exposed to X-ray films (Kodak) for two to five days at −80° C.

Hybridization of resulting blots with root RP-PCR probes "virtually subtracted" seed cDNAs shared with the root mRNA population. The remaining seed cDNAs representing putative seed-specific cDNAs, including those encoding oleosins, were sequenced by the cycle sequencing method, thereby identifying AtS21 as an oleosin cDNA clone.

Sequence analysis of AtS21

Figure 4:
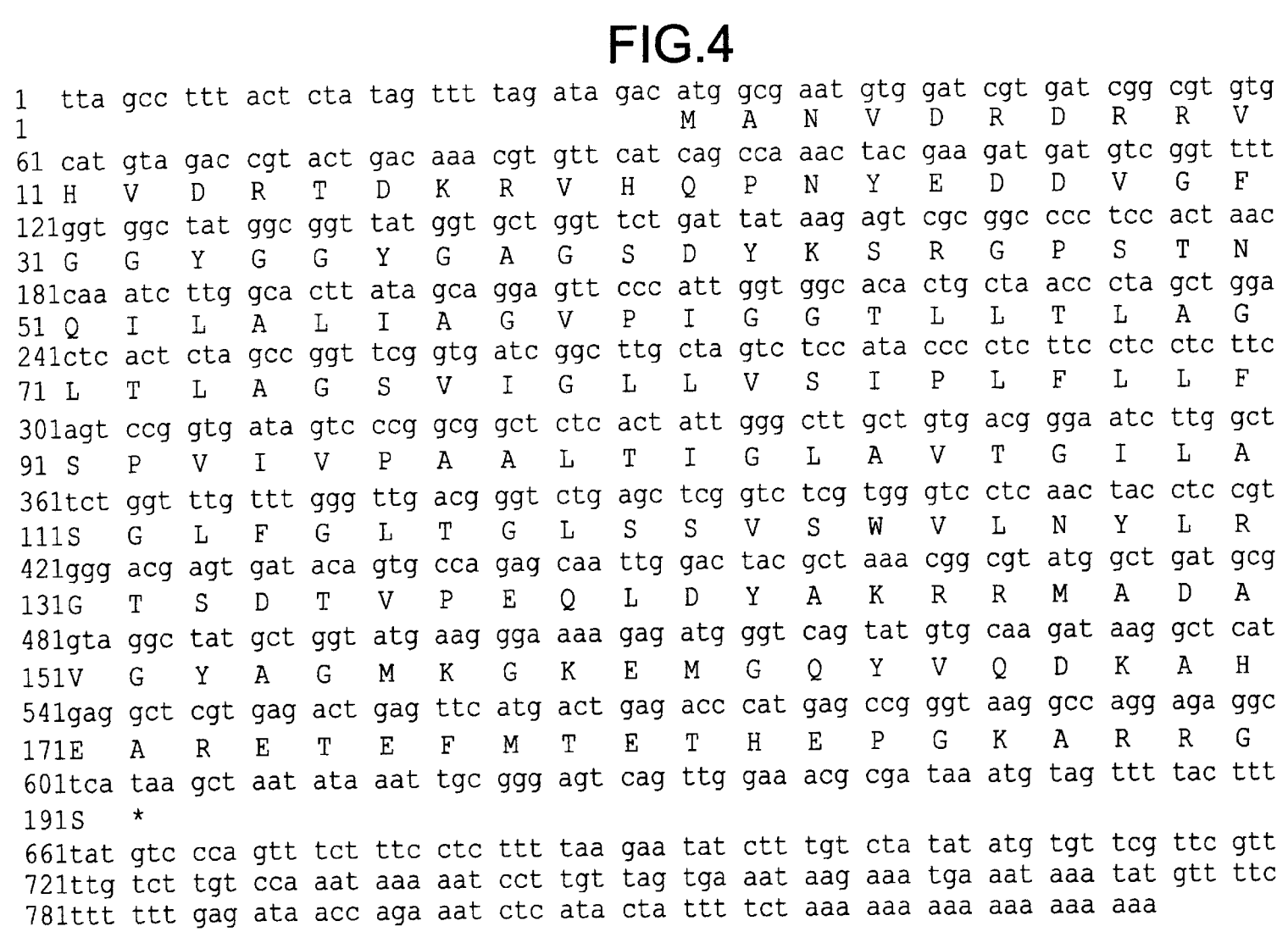
Figure 5:
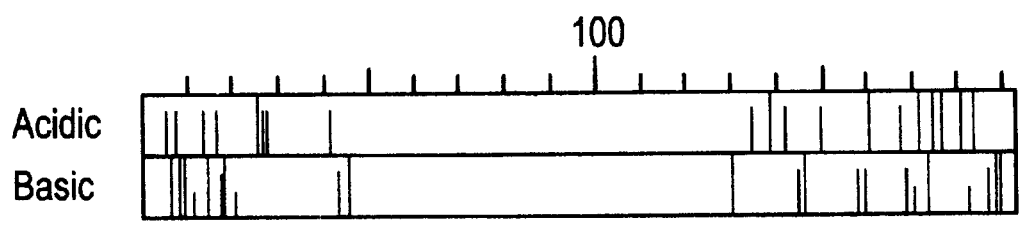
FIG. 5 is an acidic-base map of the predicted AtS21 protein generated by DNA Strider 1.2.
Figure 6:
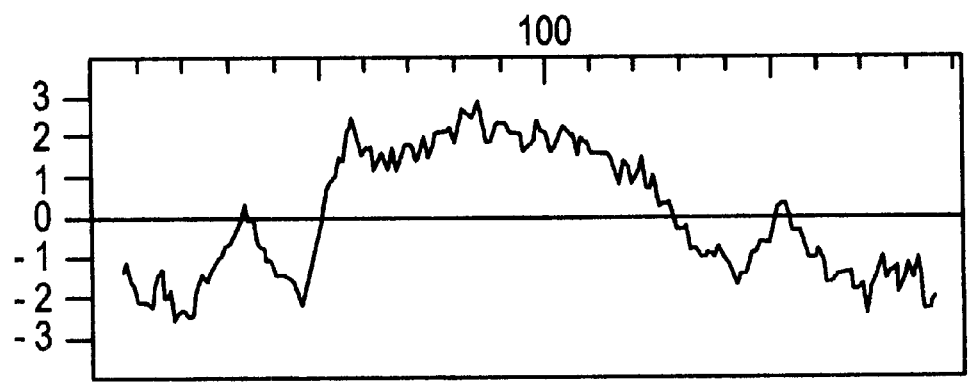
FIG. 6 is a Kyte-Doolittle plot of the predicted AtS21 protein generated by DNA Strider 1.2.

The oleosin cDNA is 834 bp long including an 18 bp long poly A tail (FIG. 4, SEQ ID NO:2) It has high homology to other oleosin genes from Arabidopsis as well as from other species. Recently, an identical oleosin gene has been reported (Zou, et al., 1996, *Plant Mol.Biol.* 31:429–433. The predicted protein is 191 amino acids long with a highly hydrophobic middle domain flanked by a hydrophilic domain on each side. The existence of two upstream in frame stop codons and the similarity to other oleosin genes indicate that this cDNA is full-length. Since there are two in frame stop codons just upstream of the first ATG, this cDNA is considered to be a full length cDNA (FIG. 4, SEQ ID NO:2). The predicted protein has three distinctive domains based on the distribution of its amino acid residues. Both the N-terminal and C-terminal domains are rich in charged residues while the central domain is absolutely hydrophobic (FIG. 5). As many as 20 leucine residues are located in the central domain and arranged as repeats with one leucine occurring every 7–10 residues. Other non-polar amino acid residues are also clustered in the central domain making this domain absolutely hydrophobic (FIG. 6).

Extensive searches of different databases using both AtS21 cDNA and its predicted protein sequence identified oleosins from carrot, maize, cotton, rapeseed, Arabidopsis, and other plant species. The homology is mainly restricted to the central hydrophobic domain. Seven Arabidopsis oleosin sequences were found. AtS21 represents the same gene as Z54164 which has a few more bases in the 5' untranslated region. The seven Arabidopsis oleosin sequences available so far were aligned to each other (FIG. 7). The result suggested that the seven sequences fall into three groups. The first group includes AtS21 (SEQ ID NO:3), X91918 (SEQ ID NO:4), and the partial sequence Z29859 (SEQ ID NO:5). Since X91918 (SEQ ID NO:4) has only its last residue different from AtS21 (SEQ ID NO:3), and since Z29859 (SEQ ID NO:5) has only three amino acid residues which are different from AtS21 (SEQ ID NO:3), all three sequences likely represent the same gene. The two sequences of the second group, X62352 (SEQ ID NO:6) and Ato13 (SEQ ID NO:7), are different in both sequence and length. Thus, there is no doubt that they represent two independent genes. Like the first group, the two sequences of the third group, X91956 (SEQ ID NO:8) and L40954 (SEQ ID NO:9), also have only three divergent residues which may be due to sequence errors. Thus, X91956 (SEQ ID NO:8) and L40954 (SEQ ID NO:9) likely represent the same gene. Unlike all the other oleosin sequences which were predicted from cDNA sequences, X62352 (SEQ ID NO:6) was deduced from a genomic sequence (Van Rooigen et al. 1992 *Plant Mol. Biol.* 18:1177–1179. In conclusion, four different Arabidopsis oleosin genes have been identified so far, and they are conserved only in the middle of the hydrophobic domain.

Northern Analysis

In order to characterize the expression pattern of the native AtS21 gene, Northern analysis was performed as described in Example 4 except that the probe was the AtS21 cDNA (pAN1 insert) labeled with $^{32}$P-DATP to a specific activity of $5 \times 10^8$ cpm/μg.

Figure 8A:
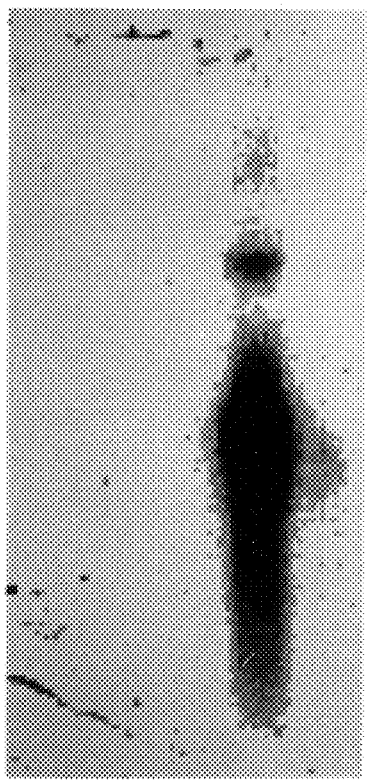
FIG. 8A is a Northern analysis of the AtS21 gene. An RNA gel blot containing ten micrograms of total RNA extracted from Arabidopsis flowers (F), leaves (L), roots (R), developing seeds (Se), and developing silique coats (Si) was hybridized with a probe made from the full-length AtS21 cDNA.
Figure 13A:
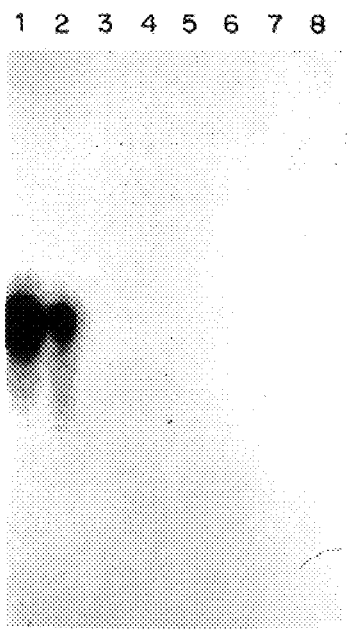
FIG. 13A is a Northern analysis showing AtS21 mRNA levels in developing wild-type Arabidopsis seedlings. Lane 1 was loaded with RNA from developing seeds, lane 2 was loaded with RNA from seeds imbibed for 24–48 hours, lane 3: 3 day seedlings; lane 4: 4 day seedlings; lane 5: 5 day seedlings; lane 6: 6 day seedlings; lane 7; 9 day seedlings; lane 8: 12 day seedlings. Probe was labeled AtS21 cDNA. Exposure was for one hour at −80° C.
Figure 13B:
FIG. 13B is the same blot as FIG. 13A only exposure was for 24 hours at −80° C.

Results indicated that the AtS21 gene is strongly expressed in developing seeds and weakly expressed in silique coats (FIG. 8A). A much larger transcript, which might represent unprocessed AtS21 pre-mRNA, was also detected in developing seed RNA. AtS21 was not detected in flower, leaf, root (FIG. 8A), or one day silique RNAs. A different Northern analysis revealed that AtS21 is also strongly expressed in imbibed germinating seeds (FIGS. 13A and 13B).

EXAMPLE 6

Characterization of Oleosin Genomic Clones and Isolation of Oleosin Promoter

Genomic clones were isolated by screening an Arabidopsis genomic DNA library using the full length cDNA (AtS21)as a probe. Two genomic clones were mapped by restriction enzyme digestion followed by Southern hybridization using the 5' half of the cDNA cleaved by SacI as a probe. A 2 kb SacI fragment was subcloned and sequenced (FIG. 9, SEQ ID NO:33). Two regions of the genomic clone are identical to the cDNA sequence. A 395 bp intron separates the two regions.

Figure 8B:
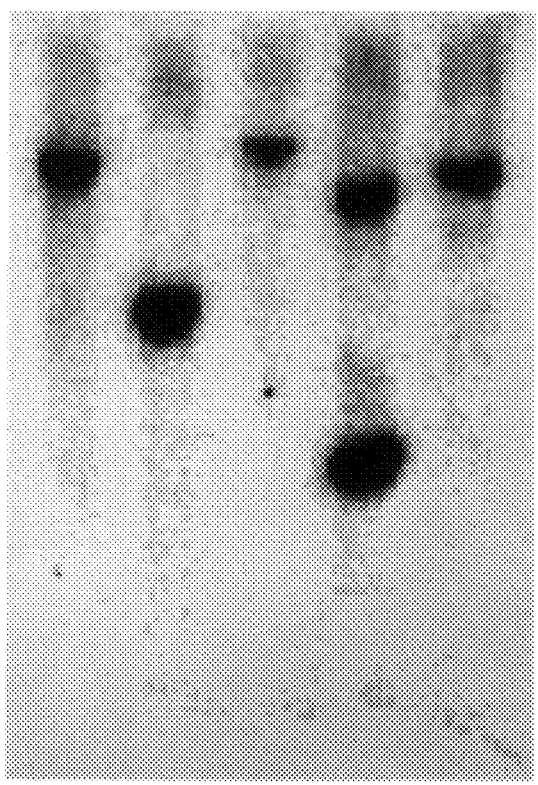
FIG. 8B is a Southern analysis of the AtS21 gene. A DNA gel blot containing ten micrograms of genomic DNA digested with BamHI (B), EcoRI (E), HindIII (H), SacI (S), and XbaI (X) was hybridized with a probe made from the full length AtS21 cDNA.

The copy number of AtS21 gene in the Arabidopsis genome was determined by genomic DNA Southern hybridization following digestion with the enzymes BamHI, EcoRI, HindIII, SacI and XbaI, using the full length cDNA as a probe (FIG. 8B). A single band was detected in all the lanes except SacI digestion where two bands were detected. Since the cDNA probe has an internal SacI site, these results indicated that AtS21 is a single copy gene in the Arabidopsis genome. Since it has been known that Arabidopsis genome contains different isoforms of oleosin genes, this Southern analysis also demonstrates that the different oleosin isoforms of Arabidopsis are divergent at the DNA sequence level.

Two regions, separated by a 395 bp intron, of the genomic DNA fragment are identical to AtS21 cDNA sequence. Database searches using the 5' promoter sequence upstream of AtS21 cDNA sequence did not identify any sequence with significant homology. Furthermore, the comparison of AtS21 promoter sequence with another Arabidopsis oleosin promoter isolated previously (Van Rooijen, et al., 1992) revealed little similarity. The AtS21 promoter sequence is rich in A/T bases, and contains as many as 44 direct repeats ranging from 10 bp to 14 bp with only one mismatch allowed. Two 14 bp direct repeats, and a putative ABA response element are underlined in FIG. 9.

EXAMPLE 7

Figure 10:
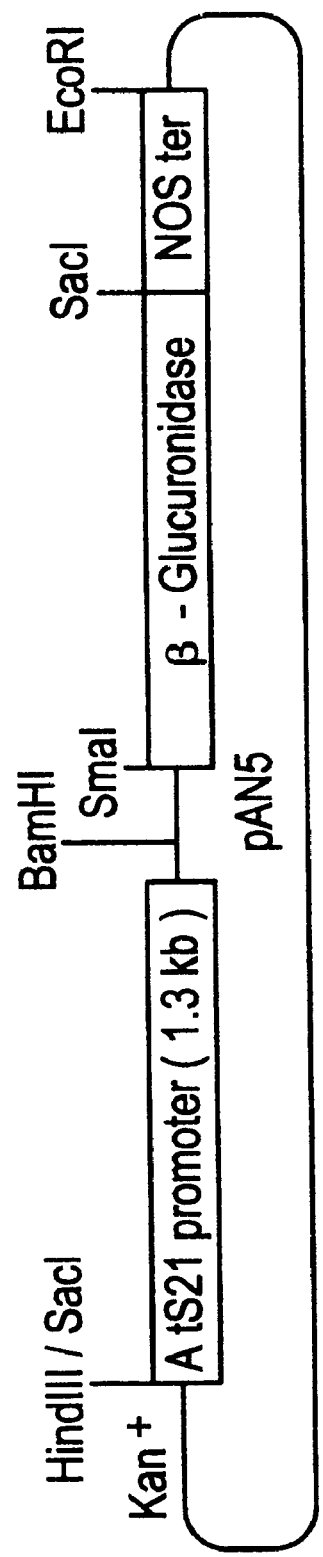
FIG. 10 is a map of AtS21 promoter/GUS construct (pAN5).

Construction of AtS21 Promoter/GUS Gene Expression Cassette and Expression Patterns in Transgenic Arabidopsis and Tobacco Construction of AtS21 promoter/GUS gene expression cassette The 1267 bp promoter fragment starting from the first G upstream of the ATG codon of the genomic DNA fragment was amplified using PCR and fused to the GUS reporter gene for analysis of its activity. The promoter fragment of the AtS21 genomic clone was amplified by PCR using the T7 primer GTAATACGACTCACTATAGGGC (SEQ ID NO:11) and the 21P primer GGGGATCCTATACTAAAAC-TATAGAGTAAAGG (SEQ ID NO:12) complementary to the 5' untranslated region upstream of the first ATG codon (FIG. 9). A BamHI cloning site was introduced by the 21P primer. The amplified fragment was cloned into the BamHI and SacI sites of pBluescript KS (Stratagene). Individual clones were sequenced to check possible PCR mutations gas well as the orientation of their inserts. The correct clone was digested with BamHI and HindIII, and the excised promoter fragment (1.3 kb) was cloned into the corresponding sites of pBI101.1 (Jefferson, R. A. 1987a, *Plant Mol. Biol. Rep.* 5:387–405; Jefferson et al., 1987b, *EMBO J.* 6:3901–3907) upstream of the GUS gene. The resultant plasmid was designated pAN5 (FIG. 10). The AtS21 promoter/GUS construct (pAN5) was introduced into both tobacco (by the leaf disc method, Horsh et al., 1985; Bogue et al. 1990 *Mol. Gen. Gen.* 221:49–57) and Arabidopsis Colombia ecotype via vacuum infiltration as described by Bechtold, et al. (1993) *C.R. Acad. Sci. Paris,* 316:1194–1199. Seeds were sterilized and selected on media containing 50 μg/ml kanamycin, 500 μg/ml carbenicillin.

GUS activity assay:

Expression patterns of the reporter GUS gene were revealed by histochemical staining (Jefferson, et al., 1987a, *Plant Mol. Biol. Rep.* 5:387–405). Different tissues were stained in substrate solution containing 2 mg/ml 5-bromo-4-chloro-3-indolyl-β-D-glucuronic acid (X-Gluc) (Research Organics, Inc.), 0.5 mM potassium ferrocyanide, and 0.5 mM potassium ferricyanide in 50 mM sodium phosphate buffer, pH 7.0 at 37° C. overnight, and then dehydrated successively in 20%, 40% and 80% ethanol (Jefferson, et al., 1987). Photographs were taken using an Axiophot (Zeiss) compound microscope or Olympus SZH10 dissecting microscope. Slides were converted to digital images using a Spring/Scan 35LE slide scanner (Polaroid) and compiled using Adobe Photoshop™ 3.0.5 and Canvas™ 3.5.

GUS activities were quantitatively measured by fluorometry using 2 mM 4-MUG (4-methylumbelliferyl-β-D-glucuronide) as substrate (Jefferson, et al., 1987). Developing Arabidopsis seeds were staged according to their colors, and other plant tissues were collected and kept at −80° C. until use. Plant tissues were ground in extraction buffer containing 50 mM sodium phosphate, pH 7.0, 10 mM EDTA, 10 mM β-mercaptoethanol, 0.1% Triton X-100, and 0.1% sodium lauryl sarcosine. The tissue debris was removed by 5 minutes centrifugation in a microfuge. The supernatant was aliquoted and mixed with substrate and incubated at 37° C. for 1 hour. Three replicas were assayed for each sample. The reactions were stopped by adding 4 volumes of 0.2 M sodium carbonate. Fluorescence was read using a TKO-100 DNA fluorometer (Hoefer Scientific Instruments). Protein concentrations of the extracts were determined by the Bradford method (Bio Rad).

Expression patterns of AtS21 promoter/GUS in transgenic Arabidopsis and tobacco

In Arabidopsis, GUS activity was detected in green seeds, and node regions where siliques, cauline leaves and branches join the inflorescence stem (FIGS. 11A and 11B). No GUS activity was detected in any leaf, root, flower, silique coat, or the internode regions of the inflorescence stem. Detailed studies of the GUS expression in developing seeds revealed that the AtS21 promoter was only active in green seeds in which the embryos had already developed beyond heart stage (FIGS. 11C and 11G). The youngest embryos showing GUS activity that could be detected by histochemical staining were at early torpedo stage. Interestingly, the staining was only restricted to the lower part of the embryo including hypocotyl and embryonic radical. No staining was detected in the young cotyledons (FIGS. 11D and 11E). Cotyledons began to be stained when the embryos were at late torpedo or even early cotyledon stage (FIGS. 11F and 11H). Later, the entire embryos were stained, and the staining became more intense as the embryos matured (FIGS. 11I and 11J). It was also observed that GUS gene expression was restricted to the embryos. Seed coat and young endosperm were not stained (FIG. 11C).

GUS activity was also detected in developing seedlings. Young seedlings of 3–5 days old were stained everywhere. Although some root hairs close to the hypocotyl were stained (FIG. 11K), most of the newly formed structures such as root hairs, lateral root primordia and shoot apex were not stained (FIGS. 11L AND 11N). Later, the staining was restricted to cotyledons and hypocotyls when lateral roots grew from the elongating embryonic root. The staining on embryonic roots disappeared. No staining was observed on newly formed lateral roots, true leaves nor trichomes on true leaves (FIGS. 11M and 11N).

AtS21 promoter/GUS expression patterns in tobacco are basically the same as in Arabidopsis. GUS activity was only detected in late stage seeds and different node regions of mature plants. In germinating seeds, strong staining was detected throughout the entire embryos as soon as one hour after they were dissected from imbibed seeds. Mature endosperm, which Arabidopsis seeds do not have, but not seed coat was also stained (FIG. 12A). The root tips of some young seedlings of one transgenic line were not stained (FIG. 12B). Otherwise, GUS expression patterns in developing tobacco seedlings were the same as in Arabidopsis seedlings (FIGS. 12B, 12C, and 12D). Newly formed structures such as lateral roots and true leaves were not stained.

AtS21 mRNA levels in developing seedlings

Figure 13C:
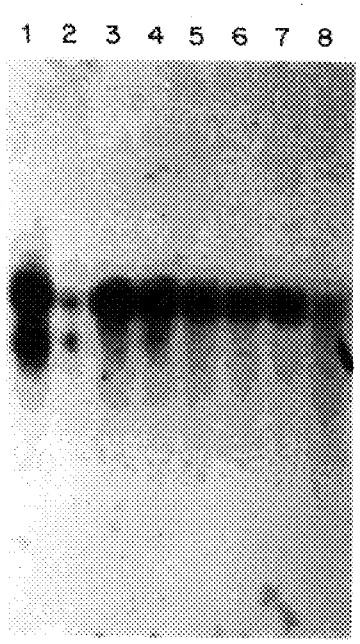
FIG. 13C is the same blot depicted in FIGS. 13A and 13B after stripping and hybridization with an Arabidopsis tubulin gene probe. The small band in each of lanes 1 and 2 is the remnant of the previous AtS21 probe. Exposure was for 48 hours at −80° C.

Since the observed strong activities of AtS21 promoter/GUS in both Arabidopsis and tobacco seedlings are not consistent with the seed-specific expression of oleosin genes, Northern analysis was carried out to determine if AtS21 mRNA was present in developing seedlings where the GUS activity was so strong. RNAs prepared from seedlings at different stages from 24 hours to 12 days were analyzed by Northern hybridization using AtS21 cDNA as the probe. Surprisingly, AtS21 mRNA was detected at a high level comparable to that in developing seeds in 24–48 hour imbibed seeds. The mRNA level dropped dramatically when young seedlings first emerged at 74 hours (FIGS. 13A and 13B). In 96 hour and older seedlings, no signal was detected even with a longer exposure (FIG. 13B). The loadings of RNA samples were checked by hybridizing the same blot with a tubulin gene probe (FIG. 13C) which was isolated and identified by EST analysis as described in Example 2. Since AtS21 mRNA was so abundant in seeds, residual AtS21 probes remained on the blot even after extensive stripping. These results indicated that AtS21 mRNA detected in imbibed seeds and very young seedlings are the carry-over of AtS21 mRNA from dry seeds. It has recently been reported that an oleosin Atol2 mRNA (identical to AtS21) is most abundant in dry seeds (Kirik, et al., 1996 *Plant Mol. Biol.* 31(2):413–417.) Similarly, the strong GUS activities in seedlings were most likely due to the carry-over of both β-glucuronidase protein and the de novo synthesis of β-glucuronidase from its mRNA carried over from the dry seed stage.

EXAMPLE 8

Activity comparison between the AtS21 promoter and the 35S promoter

The GUS activities in transgenic Arabidopsis developing seeds expressed by the AtS21 promoter were compared with those expressed by the 35S promoter in the construct pBI221 (Jefferson et al. *EMBO J.* 6:3901–3907). The seeds were staged according to their colors (Table 2). The earliest stage was from globular to late heart stage when the seeds were still white but large enough to be dissected from the siliques.

Figure 14:
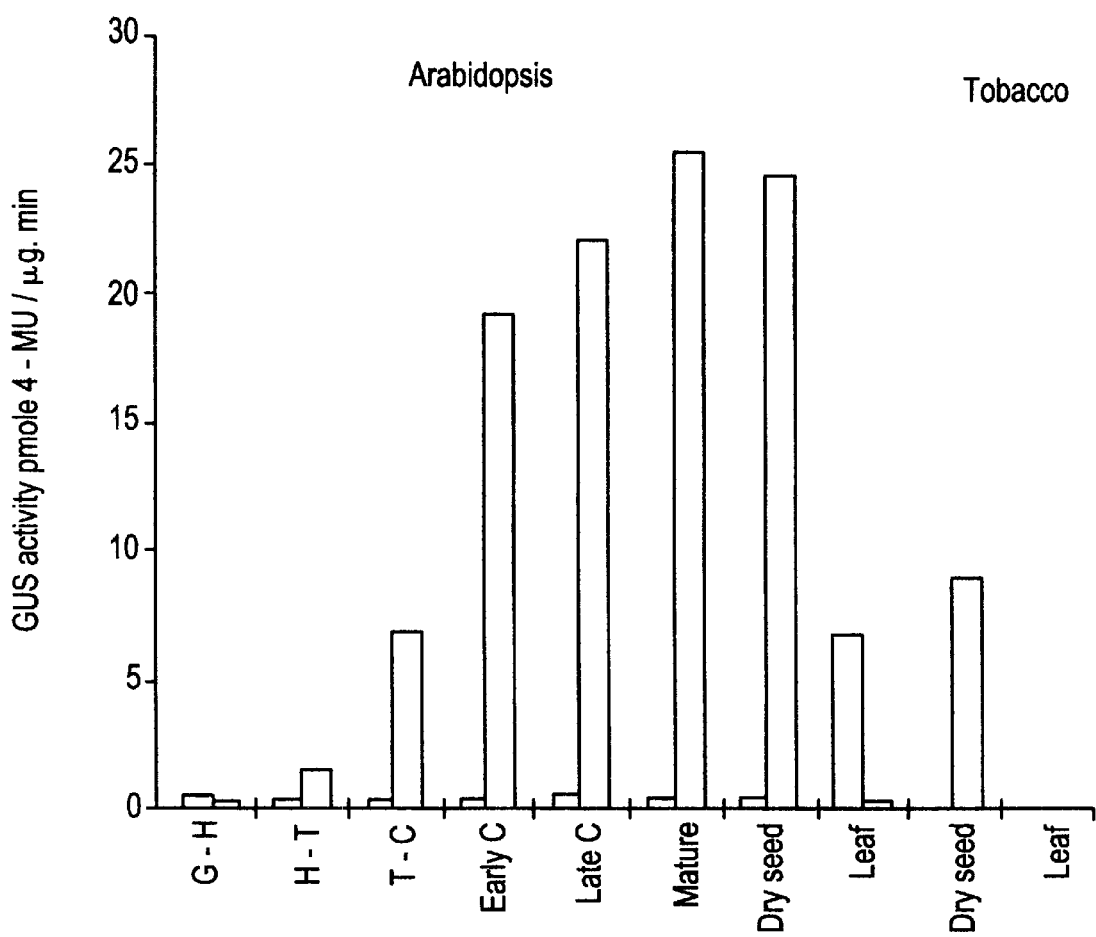
FIG. 14 is a graph comparing GUS activities expressed by the AtS21 and 35S promoters. GUS activities expressed by the AtS21 promoter in developing Arabidopsis seeds and leaf are plotted side by side with those expressed by the 35S promoter. The GUS activities expressed by the AtS21 promoter in tobacco dry seed and leaf are plotted on the right side of the figure. GUS activity in tobacco leaf is so low that no column appears. "G-H" denotes globular to heart stage; "H-T" denotes heart to torpedo stage; "T-C" denotes torpedo to cotyledon stage; "Early C" denotes early cotyledon; "Late C" denotes late cotyledon. The standard deviations are listed in Table 2.

AtS21 promoter activity was detected at a level about three times lower than that of the 35S promoter at this stage. 35S promoter activity remained at the same low level throughout the entire embryo development. In contrast, AtS21 promoter activity increased quickly as the embryos passed torpedo stage and reached the highest level of 25.25 pmole 4-MU/ min. μg protein at mature stage (FIGS. 5–8). The peak activity of the AtS21 promoter is as much as 210 times higher than its lowest activity at globular to heart stage, and is close to 100 times higher than the 35S promoter activity at the same stage (Table 2). The activity levels of the AtS21 promoter are similar to those of another Arabidopsis oleosin promoter expressed in *Brassica napus* (Plant et al. 1994, *Plant mol. Biol.* 25:193–205. AtS21 promoter activity was also detected at background level in leaf. The high standard deviation, higher than the average itself, indicated that the GUS activity was only detected in the leaves of some lines (Table 2). On the other hand, 35S promoter activity in leaf was more than 20 times higher than that in seed. The side by side comparisons of activities between AtS21 promoter and 35S promoter is shown in FIG. 14.

Although the AtS21 promoter activity was about 3 times lower in dry seed of tobacco than in Arabidopsis dry seed, the absolute GUS activity was still higher than that expressed by the 35S promoter in Arabidopsis leaf (Table 2). No detectable AtS21 promoter activity was observed in tobacco leaf (FIG. 14).

Comparison of the AtS21 promoter versus the 35S promoter revealed that the latter is not a good promoter to express genes at high levels in developing seeds. Because of its consistent low activities throughout the entire embryo development period, 35S promoter is useful for consistent low level expression of target genes. On the other hand, the AtS21 promoter is a very strong promoter that can be used to express genes starting from heart stage embryos and accumulating until the dry seed stage. The 35S promoter, although not efficient, is better than the AtS21 promoter in expressing genes in embryos prior to heart stage.

EXAMPLE 9

Expression of the Borage $\Delta^6$-Desaturase Gene Under the Control of the AtS21 Promoter and Comparison to Expression Under the Control of the CaMV 35S Promoter In order to create an expression construct with the AtS21 promoter driving expression of the borage Δ6-desaturase gene, the GUS coding fragment from pAN5 was removed by digestion with SmaI and EcoICR I. The cDNA insert of pAN1 (Example 2) was then excised by first digesting with XhoI (and filling in the residual overhang as above), and then digesting with SmaI. The resulting fragment was used to replace the excised portion of pAN5, yielding pAN3.

Levels of $\Delta^6$-desaturase activity were monitored by assaying the corresponding fatty acid methyl esters of its reaction products, γ-linolenic acid (GLA) and octadecatetraenoic acid (OTA) using the methods referred to in Example 3. The GLA and OTA levels (Table 3) of the transgenic seeds ranged up to 6.7% of C18 fatty acids (Mean=3.1%) and 2.8% (Mean=1.1%), respectively. No GLA or OTA was detected in the leaves of these plants. In comparison, CaMV 35 S promoter/$\Delta^6$-desaturase transgenic plants produced GLA levels in seeds ranging up to 3.1% of C18 fatty acids (Mean=1.3%) and no measurable OTA in seeds.

TABLE 1

COMPARISON OF COMMON AMINO ACID MOTIFS IN MEMBRANE-BOUND DESATURASES

| Desaturase | Lipid Box | Metal Box 1 | Metal Box 2 |
| --- | --- | --- | --- |
| Borage $\Delta^6$ | WIGHDAGH (SEQ. ID. NO:13) | HNAHH (SEQ. ID. NO:19) | FQIEHH (SEQ. ID. NO:27) |
| Synechocystis $\Delta^6$ | NVGHDANH (SEQ. ID. NO:14) | HNYLNH (SEQ. ID. NO:20) | HQVTHH (SEQ. ID. NO:28) |
| Arab. chloroplast $\Delta^{15}$ | VLGHDCGH (SEQ. ID. NO:15) | HRTHH (SEQ. ID. NO:21) | HVIHH (SEQ. ID. NO:29) |
| Rice $\Delta^{15}$ | VLGHDCGH (SEQ. ID. NO:15) | HRTHH (SEQ. ID. NO:21) | HVIHH (SEQ. ID. NO:29) |
| Glycine chloroplast $\Delta^{15}$ | VLGHDCGH (SEQ. ID. NO:15) | HRTHH (SEQ. ID. NO:21) | HVIHH (SEQ. ID. NO:29) |
| Arab. fad3 ($\Delta^{15}$) | VLGHDCGH (SEQ. ID. NO:15) | HRTHH (SEQ. ID. NO:21) | HVIHH (SEQ. ID. NO:29) |
| Brassica fad 3 ($\Delta^{15}$) | VLGHDCGH (SEQ. ID. NO:15) | HRTHH (SEQ. ID. NO:21) | HVIHH (SEQ. ID. NO:29) |
| Borage $\Delta^{12}$ (P1–81)* | VIAHEGGH (SEQ. ID. NO:16) | HRRHH (SEQ. ID. NO:22) | HVAHH (SEQ. ID. NO:30) |
| Arab. fad2 ($\Delta^{12}$) | VIAHECGH (SEQ. ID. NO:16) | HRRHH (SEQ. ID. NO:22) | HVAHH (SEQ. ID. NO:30) |
| Arab. chloroplast $\Delta^{12}$ | VIGHDCAH (SEQ. ID. NO:17) | HDRHH (SEQ. ID. NO:23) | HIPHH (SEQ. ID. NO:31) |
| Glycine plastid $\Delta^{12}$ | VIGHDCAH (SEQ. ID. NO:17) | HDRHH (SEQ. ID. NO:23) | HIPHH (SEQ. ID. NO:31) |
| Spinach plastidial n-6 | VIGHDCAH (SEQ. ID. NO:17) | HDQHH (SEQ. ID. NO:24) | HIPHH (SEQ. ID. NO:31) |
| Synechocystis $\Delta^{12}$ | VVGHDCGH (SEQ. ID. NO:18) | HDHHH (SEQ. ID. NO:25) | HIPHH (SEQ. ID NO:31) |
| Anabaena $\Delta^{12}$ | VLGHDCGH (SEQ. ID. NO:15) | HHHHH (SEQ. ID. NO:26) | HVPHH (SEQ. ID. NO:32) |

*P1–81 is a full length cDNA which was identified by EST analysis and shows high similarity to the Arbidopsis Δ12 desaturase (fad2)

TABLE 2

GUS ACTIVITIES OF AtS21 and 35S PROMOTER/GUS CONSTRUCTS

| COLOR STAGE | WHITE G—H | WHITE/YELLOW H—T | YELLOW T—C | LIGHT GREEN EARLY C | DARK GREEN LATE C | GREEN/ YELLOW/BROWN MATURE | BROWN DRY SEED | LEAF |
| --- | --- | --- | --- | --- | --- | --- | --- | --- |
| AtS21 | 0.12 ± 0.17 | 1.35 ± 1.57 | 6.77 ± 1.25 | 18.99 ± 3.75 | 21.85 ± 4.45 | 25.25 ± 4.64 | 24.38 ± 10.85 | 0.08 ± 0.1 |
| 35S | 0.30 ± 0.06 | 0.25 ± 0.08 | 0.29 ± 0.04 | 0.28 ± 0.03 | 0.33 ± 0.06 | 0.26 ± 0.04 | 0.31 ± 0.02 | 6.56 ± 0.7 |
| AtS21 | (In tobacco) | | | | | | 8.81 ± 0.21 | 0.01 ± 0.0 |

Abbreviations: G, globular stage; H, heart stage; T, torpedo stage; C, cotyledon stage. The GUS activities are in pmole 4-MU/$\mu$g protein.min. For AtS21 promoter the numbers are the average of five independent lines with standard deviations. Three repeats were assayed for each line. For 35S promoter the numbers are the average of three repeats of the same line with standard deviations.

TABLE 3

EXPRESSION OF THE BORAGE $\Delta^{6-DESATURASE}$ IN TRANSGENIC PLANTS

| | | SEED | | | | LEAF | | |
| --- | --- | --- | --- | --- | --- | --- | --- | --- |
| PROMOTER | PLANT | GLA* | RANGE | OTA* | RANGE | GLA | RANGE | OTA | RANGE |
| Cauliflower mosaic virus 35S | tobacco | 1.3 | 0.7–3.1 | n.d | | 20 | 19–22 | 9.7 | 8–11 |
| Arabidopsis oleosin | Arabidopsis | 3.1 | 0–6.7 | 1.1 | 0–2.8 | n.d. | | n.d | |

*mean value expressed as the percent of the $C_{18}$ fatty acids
n.d. not detected

What is claimed is:

1. An isolated nucleic acid corresponding to an oleosin 5' regulatory region which directs seed-specific expression comprising the nucleotide sequence set forth in SEQ ID NO:10.

2. An expression cassette which comprises an oleosin 5' regulatory region which directs seed-specific expression, said 5' regulatory region comprising the nucleotide sequence set forth in SEQ ID NO:10 wherein said oleosin 5' regulatory region is operably linked to at least one of a nucleic acid encoding a heterologous gene or a nucleic acid encoding a sequence complementary to a native plant gene.

3. The expression cassette of claim 2 wherein the heterologous gene is at least one of a fatty acid synthesis gene or a lipid metabolism gene.

4. The expression cassette of claim 3 wherein the heterologous gene is selected from the group consisting of an acetyl-coA carboxylase gene, a ketoacyl synthase gene, a malonyl transacylase gene, a lipid desaturase gene, an acyl carrier protein (ACP) gene, a thioesterase gene, an acetyl transacylase gene, and an elongase gene.

5. The expression cassette of claim 4 wherein the lipid desaturase gene is selected from the group consisting of a Δ6-desaturase gene, a Δ12-desaturase gene, and a Δ15-desaturase gene.

6. An expression vector which comprises the expression cassette of any one of claims 2–5.

7. A cell comprising the expression cassette of any one of claims 2–5.

8. A cell comprising the expression vector of claim 6.

9. The cell of claim 7 wherein said cell is a bacterial cell or a plant cell.

10. The cell of claim 8 wherein said cell is a bacterial cell or a plant cell.

11. A transgenic plant comprising the expression cassette of any one of claims 2–5.

12. A transgenic plant comprising the expression vector of claim 6.

13. A plant which has been regenerated from the plant cell of claim 9.

14. A plant which has been regenerated from the plant cell of claim 10.

15. The plant of claim 12 wherein said plant is at least one of a sunflower, soybean, maize, cotton, tobacco, peanut, oil seed rape or Arabidopisis plant.

16. The plant of claim 13 wherein said plant is at least one of a sunflower, soybean, maize, cotton, tobacco, peanut, oil seed rape or Arabidopisis plant.

17. Transgenic progeny of the plant of claim 11.

18. Transgenic progeny of the plant of claim 12.

19. Seed from the plant of claim 11.

20. Seed from the plant of claim 12.

21. A method of producing a plant with increased levels of a product of a fatty acid synthesis gene or a lipid metabolism gene said method comprising:

(a) transforming a plant cell with an expression vector comprising an oleosin 5' regulatory region which directs seed-specific expression wherein said 5' regulatory region comprises the nucleotide sequence set forth in SEQ ID NO:10 and wherein said oleosin 5' regulatory region is operably linked to at least one of an isolated nucleic acid coding for a fatty acid synthesis gene or a lipid metabolism gene; and (b) regenerating a plant with increased levels of the product of said fatty acid synthesis or said lipid metabolism gene from said plant cell.

22. A method of producing a plant with increased levels of gamma linolenic acid (GLA) content said method comprising:
   (a) transforming a plant cell with an expression vector comprising an oleosin 5' regulatory region which directs seed-specific expression wherein said 5' regulatory region comprises the nucleotide sequence set forth in SEQ ID NO:10 and wherein said oleosin 5' regulatory region is operably linked to a Δ6-desaturase gene; and
   (b) regenerating a plant with increased levels of GLA from said plant cell.

23. The method of claim 22 wherein said Δ6-desaturase gene is at least one of a cyanobacterial Δ6-desaturase gene or a borage Δ6-desaturase gene.

24. The method of any one of claims 21–23 wherein said plant is a sunflower, soybean, maize, tobacco, cotton, peanut, oil seed rape or Arabidopsis plant.

25. The method of claim 21 wherein said fatty acid synthesis gene or said lipid metabolism gene is at least one of a lipid desaturase, an acyl carrier protein (ACP) gene, a thioesterase gene an elongase gene, an acetyl transacylase gene, an acetyl-coA carboxylase gene, a ketoacyl synthase gene, or a malonyl transacylase gene.

26. A method of inducing production of at least one of gamma linolenic acid (GLA) or octadecatetraeonic acid (OTA) in a plant deficient or lacking in GLA said method comprising:
   (a) transforming said plant with an expression vector comprising an oleosin 5' regulatory region which directs seed-specific expression, wherein said 5' regulatory region comprises the nucleotide sequence set forth in SEQ ID NO:10 and wherein said oleosin 5' regulatory region is operably linked to a Δ6-desaturase gene; and
   (b) regenerating a plant with increased levels of at least one of GLA or OTA.

27. A method of decreasing production of a fatty acid synthesis or lipid metabolism gene in a plant said method comprising:
   (a) transforming a cell of the plant with an expression vector comprising an oleosin 5' regulatory region which directs seed-specific expression wherein said 5' regulatory region comprises the nucleotide sequence set forth in SEQ ID NO:10 and wherein said oleosin 5' regulatory region is operably linked to a nucleic acid sequence complementary to a fatty acid synthesis or lipid metabolism gene; and
   (b) regenerating a plant with decreased production of said fatty acid synthesis or said lipid metabolism gene.

28. A method of cosuppressing a native fatty acid synthesis or lipid metabolism gene in a plant said method comprising:
   (a) transforming a cell of the plant with an expression vector comprising an oleosin 5' regulatory region which directs seed-specific expression wherein said 5' regulatory region comprises the nucleotide sequence set forth in SEQ ID NO:10 and wherein said oleosin 5' regulatory region is operably linked to a nucleic acid sequence encoding a fatty acid synthesis or lipid metabolism gene native to the plant; and
   (b) regenerating a plant with decreased production of said fatty acid synthesis or said lipid metabolism gene.

* * * * *

UNITED STATES PATENT AND TRADEMARK OFFICE
CERTIFICATE OF CORRECTION

PATENT NO. : 5,977,436
DATED : November 2, 1999
INVENTOR(S) : Terry L. Thomas et al.

It is certified that error appears in the above-identified patent and that said Letters Patent is hereby corrected as shown below:

Column 19, TABLE 1:
Line 42, "VIAHEGGH" should read -- VIAHECGH --.

Column 20, TABLE 1:
Line 36, "HNYLNH" should read -- HNYLHH --.
Line 48, "HHHHH" should read -- HNHHH --.

Column 22, TABLE 2:
Line 6, "0.1" should read -- 0.12 --.
Line 7, "0.7" should read -- 0.74 --.

Signed and Sealed this

Twenty-seventh Day of November, 2001

Attest:

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 1684 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 43..1387

(xi) SEQUENCE DESCRIPTION: SEQ ID NO:1:

```
ATATCTGCCT ACCCTCCCAA AGAGAGTAGT CATTTTTCAT CA ATG GCT GCT CAA        54
                                              Met Ala Ala Gln
                                               1

ATC AAG AAA TAC ATT ACC TCA GAT GAA CTC AAG AAC CAC GAT AAA CCC      102
Ile Lys Lys Tyr Ile Thr Ser Asp Glu Leu Lys Asn His Asp Lys Pro
 5              10                  15                  20

GGA GAT CTA TGG ATC TCG ATT CAA GGG AAA GCC TAT GAT GTT TCG GAT      150
Gly Asp Leu Trp Ile Ser Ile Gln Gly Lys Ala Tyr Asp Val Ser Asp
                25                  30                  35

TGG GTG AAA GAC CAT CCA GGT GGC AGC TTT CCC TTG AAG AGT CTT GCT      198
Trp Val Lys Asp His Pro Gly Gly Ser Phe Pro Leu Lys Ser Leu Ala
            40                  45                  50

GGT CAA GAG GTA ACT GAT GCA TTT GTT GCA TTC CAT CCT GCC TCT ACA      246
Gly Gln Glu Val Thr Asp Ala Phe Val Ala Phe His Pro Ala Ser Thr
        55                  60                  65

TGG AAG AAT CTT GAT AAG TTT TTC ACT GGG TAT TAT CTT AAA GAT TAC      294
Trp Lys Asn Leu Asp Lys Phe Phe Thr Gly Tyr Tyr Leu Lys Asp Tyr
```

-continued

|  |  | 70 |  |  |  | 75 |  |  |  | 80 |  |  |  |  |
|---|---|---|---|---|---|---|---|---|---|---|---|---|---|---|
| TCT | GTT | TCT | GAG | GTT | TCT | AAA | GAT | TAT | AGG | AAG | CTT | GTG | TTT | GAG | TTT | 342
| Ser | Val | Ser | Glu | Val | Ser | Lys | Asp | Tyr | Arg | Lys | Leu | Val | Phe | Glu | Phe |
| 85 |  |  |  |  | 90 |  |  |  |  | 95 |  |  |  |  | 100 |

```
TCT AAA ATG GGT TTG TAT GAC AAA AAA GGT CAT ATT ATG TTT GCA ACT      390
Ser Lys Met Gly Leu Tyr Asp Lys Lys Gly His Ile Met Phe Ala Thr
            105                 110                 115

TTG TGC TTT ATA GCA ATG CTG TTT GCT ATG AGT GTT TAT GGG GTT TTG      438
Leu Cys Phe Ile Ala Met Leu Phe Ala Met Ser Val Tyr Gly Val Leu
        120                 125                 130

TTT TGT GAG GGT GTT TTG GTA CAT TTG TTT TCT GGG TGT TTG ATG GGG      486
Phe Cys Glu Gly Val Leu Val His Leu Phe Ser Gly Cys Leu Met Gly
    135                 140                 145

TTT CTT TGG ATT CAG AGT GGT TGG ATT GGA CAT GAT GCT GGG CAT TAT      534
Phe Leu Trp Ile Gln Ser Gly Trp Ile Gly His Asp Ala Gly His Tyr
150                 155                 160

ATG GTA GTG TCT GAT TCA AGG CTT AAT AAG TTT ATG GGT ATT TTT GCT      582
Met Val Val Ser Asp Ser Arg Leu Asn Lys Phe Met Gly Ile Phe Ala
165                 170                 175                 180

GCA AAT TGT CTT TCA GGA ATA AGT ATT GGT TGG TGG AAA TGG AAC CAT      630
Ala Asn Cys Leu Ser Gly Ile Ser Ile Gly Trp Trp Lys Trp Asn His
            185                 190                 195

AAT GCA CAT CAC ATT GCC TGT AAT AGC CTT GAA TAT GAC CCT GAT TTA      678
Asn Ala His His Ile Ala Cys Asn Ser Leu Glu Tyr Asp Pro Asp Leu
        200                 205                 210

CAA TAT ATA CCA TTC CTT GTT GTG TCT TCC AAG TTT TTT GGT TCA CTC      726
Gln Tyr Ile Pro Phe Leu Val Val Ser Ser Lys Phe Phe Gly Ser Leu
    215                 220                 225

ACC TCT CAT TTC TAT GAG AAA AGG TTG ACT TTT GAC TCT TTA TCA AGA      774
Thr Ser His Phe Tyr Glu Lys Arg Leu Thr Phe Asp Ser Leu Ser Arg
230                 235                 240

TTC TTT GTA AGT TAT CAA CAT TGG ACA TTT TAC CCT ATT ATG TGT GCT      822
Phe Phe Val Ser Tyr Gln His Trp Thr Phe Tyr Pro Ile Met Cys Ala
245                 250                 255                 260

GCT AGG CTC AAT ATG TAT GTA CAA TCT CTC ATA ATG TTG TTG ACC AAG      870
Ala Arg Leu Asn Met Tyr Val Gln Ser Leu Ile Met Leu Leu Thr Lys
            265                 270                 275

AGA AAT GTG TCC TAT CGA GCT CAG GAA CTC TTG GGA TGC CTA GTG TTC      918
Arg Asn Val Ser Tyr Arg Ala Gln Glu Leu Leu Gly Cys Leu Val Phe
        280                 285                 290

TCG ATT TGG TAC CCG TTG CTT GTT TCT TGT TTG CCT AAT TGG GGT GAA      966
Ser Ile Trp Tyr Pro Leu Leu Val Ser Cys Leu Pro Asn Trp Gly Glu
    295                 300                 305

AGA ATT ATG TTT GTT ATT GCA AGT TTA TCA GTG ACT GGA ATG CAA CAA      1014
Arg Ile Met Phe Val Ile Ala Ser Leu Ser Val Thr Gly Met Gln Gln
310                 315                 320

GTT CAG TTC TCC TTG AAC CAC TTC TCT TCA AGT GTT TAT GTT GGA AAG      1062
Val Gln Phe Ser Leu Asn His Phe Ser Ser Ser Val Tyr Val Gly Lys
325                 330                 335                 340

CCT AAA GGG AAT AAT TGG TTT GAG AAA CAA ACG GAT GGG ACA CTT GAC      1110
Pro Lys Gly Asn Asn Trp Phe Glu Lys Gln Thr Asp Gly Thr Leu Asp
            345                 350                 355

ATT TCT TGT CCT CCT TGG ATG GAT TGG TTT CAT GGT GGA TTG CAA TTC      1158
Ile Ser Cys Pro Pro Trp Met Asp Trp Phe His Gly Gly Leu Gln Phe
        360                 365                 370

CAA ATT GAG CAT CAT TTG TTT CCC AAG ATG CCT AGA TGC AAC CTT AGG      1206
Gln Ile Glu His His Leu Phe Pro Lys Met Pro Arg Cys Asn Leu Arg
    375                 380                 385

AAA ATC TCG CCC TAC GTG ATC GAG TTA TGC AAG AAA CAT AAT TTG CCT      1254
Lys Ile Ser Pro Tyr Val Ile Glu Leu Cys Lys Lys His Asn Leu Pro
```

```
                390               395               400
TAC AAT TAT GCA TCT TTC TCC AAG GCC AAT GAA ATG ACA CTC AGA ACA       1302
Tyr Asn Tyr Ala Ser Phe Ser Lys Ala Asn Glu Met Thr Leu Arg Thr
405                 410                 415                 420

TTG AGG AAC ACA GCA TTG CAG GCT AGG GAT ATA ACC AAG CCG CTC CCG       1350
Leu Arg Asn Thr Ala Leu Gln Ala Arg Asp Ile Thr Lys Pro Leu Pro
                425                 430                 435

AAG AAT TTG GTA TGG GAA GCT CTT CAC ACT CAT GGT T AAAATTACCC          1397
Lys Asn Leu Val Trp Glu Ala Leu His Thr His Gly
                440                 445

TTAGTTCATG TAATAATTTG AGATTATGTA TCTCCTATGT TTGTGTCTTG TCTTGGTTCT     1457

ACTTGTTGGA GTCATTGCAA CTTGTCTTTT ATGGTTTATT AGATGTTTTT TAATATATTT     1517

TAGAGGTTTT GCTTTCATCT CCATTATTGA TGAATAAGGA GTTGCATATT GTCAATTGTT     1577

GTGCTCAATA TCTGATATTT TGGAATGTAC TTTGTACCAC GTGGTTTTCA GTTGAAGCTC     1637

ATGTGTACTT CTATAGACTT TGTTTAAATG GTTATGTCAT GTTATTT                   1684

(2) INFORMATION FOR SEQ ID NO:2:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

TTAGCCTTTA CTCTATAGTT TTAGATAGAC ATGGCGAATG TGGATCGTGA TCGGCGTGTG    60

(2) INFORMATION FOR SEQ ID NO:3:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Ala Asn Val Asp Arg Asp Arg Arg Val His Val Asp Arg Thr Asp
1               5                   10                  15

Lys Arg Val His Gln Pro Asn Tyr Glu Asp Val Gly Phe Gly Gly
            20                  25                  30

Tyr Gly Gly Tyr Gly Ala Gly Ser Asp Tyr Lys Ser Arg Gly Pro Ser
        35                  40                  45

Thr Asn Gln Ile Leu Ala Leu Ile Ala Gly Val Pro Ile Gly Gly Thr
    50                  55                  60

Leu Ile Thr Leu Ala Gly Leu Thr Leu Ala Gly Ser Val Ile Gly Ile
65                  70                  75                  80

Ile Val Ser Ile Pro Ile Phe Leu Ile Phe Ser Pro Val Ile Val Pro
                85                  90                  95

Ala Ala Leu Thr Ile Gly Leu Ala Val Thr Gly Ile Leu Ala Ser Gly
                100                 105                 110

Leu Phe Gly Leu Thr Gly Leu Ser Ser Val Ser Trp Val Leu Asn Tyr
            115                 120                 125

Leu Arg Gly Thr Ser Asp Thr Val Pro Glu Gln Leu Asp Tyr Ala Lys
        130                 135                 140

Arg Arg Met Ala Asp Ala Val Gly Tyr Ala Gly Met Lys Gly Lys Glu
```

```
145                150                 155                160
Met Gly Gln Tyr Val Gln Asp Lys Ala His Glu Ala Arg Glu Thr Glu
                    165                 170                 175

Phe Met Thr Glu Thr His Glu Pro Gly Lys Ala Arg Arg Gly Ser
                180                 185                 190
```

(2) INFORMATION FOR SEQ ID NO:4:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Asn Val Asp Arg Asp Arg Arg Val His Val Asp Arg Thr Asp
1                   5                  10                  15

Lys Arg Val His Gln Pro Asn Tyr Glu Asp Val Gly Phe Gly Gly
                20                  25                  30

Tyr Gly Gly Tyr Gly Ala Gly Ser Asp Tyr Lys Ser Arg Gly Pro Ser
            35                  40                  45

Thr Asn Gln Ile Leu Ala Leu Ile Ala Gly Val Pro Ile Gly Gly Thr
50                  55                  60

Leu Ile Thr Leu Ala Gly Leu Thr Leu Ala Gly Ser Val Ile Gly Ile
65                  70                  75                  80

Ile Val Ser Ile Pro Leu Phe Leu Ile Phe Ser Pro Val Ile Val Pro
                85                  90                  95

Ala Ala Ile Thr Ile Gly Leu Ala Val Thr Gly Ile Leu Ala Ser Gly
                100                 105                 110

Leu Phe Gly Leu Thr Gly Leu Ser Ser Val Ser Trp Val Leu Asn Tyr
            115                 120                 125

Leu Arg Gly Thr Ser Asp Thr Val Pro Glu Gln Leu Asp Tyr Ala Lys
    130                 135                 140

Arg Arg Met Ala Asp Ala Val Gly Tyr Ala Gly Met Lys Gly Lys Glu
145                 150                 155                 160

Met Gly Gln Tyr Val Gln Asp Lys Ala His Glu Ala Arg Glu Thr Glu
                    165                 170                 175

Phe Met Thr Glu Thr His Glu Pro Gly Lys Ala Arg Arg Gly Pro
                180                 185                 190
```

(2) INFORMATION FOR SEQ ID NO:5:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Phe Gly Leu Thr Gly Leu Ser Ser Val Ser Trp Val Leu Gln Leu Pro
1                   5                  10                  15

Pro Trp Ala Ser Asp Thr Val Pro Glu Gln Val Asp Tyr Ala Lys Arg
                20                  25                  30

Arg Met Ala Asp Ala Val Gly Tyr Ala Gly Met Lys Gly Lys Glu Met
            35                  40                  45

Gly Gln Tyr Val Gln Asp Lys Ala His Glu Ala Arg Glu Thr Glu Phe
```

```
                50                    55                    60
Met Thr Glu Thr His Glu Pro Gly Lys Ala Arg Arg Gly Ser
 65                    70                    75
```

(2) INFORMATION FOR SEQ ID NO:6:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
                20                  25                  30

Arg Gly Ser Asp Tyr Ser Lys Ser Arg Gln Ile Ala Lys Ala Ala Thr
            35                  40                  45

Ala Val Thr Ala Gly Gly Ser Leu Leu Val Leu Ser Leu Thr Leu
        50                  55                  60

Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                    85                  90                  95

Thr Gly Phe Leu Ser Ser Gly Gly Phe Gly Ile Ala Ala Ile Thr Val
                100                 105                 110

Phe Ser Trp Ile Tyr Lys Tyr Ala Thr Gly Glu His Pro Gln Gly Ser
            115                 120                 125

Asp Lys Leu Asp Ser Ala Arg Met Lys Leu Gly Ser Lys Ala Gln Asp
        130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170
```

(2) INFORMATION FOR SEQ ID NO:7:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Ala Asp Gln Thr Arg Thr His His Glu Met Ile Ser Arg Asp Ser
 1               5                  10                  15

Thr Gln Glu Ala His Pro Lys Ala Arg Gln Met Val Lys Ala Ala Thr
                20                  25                  30

Ala Val Thr Ala Gly Gly Ser Leu Leu Val Leu Ser Gly Leu Thr Leu
            35                  40                  45

Ala Gly Thr Val Ile Ala Leu Thr Val Ala Thr Pro Leu Leu Val Ile
        50                  55                  60

Phe Ser Pro Val Leu Val Pro Ala Val Val Thr Val Ala Leu Ile Ile
 65                  70                  75                  80

Thr Gly Phe Leu Ala Ser Gly Gly Phe Gly Ile Ala Ala Ile Thr Ala
```

```
                    85                  90                  95
Phe Ser Trp Leu Tyr Arg His Met Thr Gly Ser Gly Ser Asp Lys Ile
            100                 105                 110
Glu Asn Ala Arg Met Lys Val Gly Ser Arg Val Gln Asp Thr Lys Tyr
            115                 120                 125
Gly Gln His Asn Ile Gly Val Gln His Gln Gln Val Ser
        130                 135                 140

(2) INFORMATION FOR SEQ ID NO:8:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Ala Asp Thr His Arg Val Asp Arg Thr Asp Arg His Phe Gln Phe
1               5                   10                  15
Gln Ser Pro Tyr Glu Gly Gly Arg Gly Gln Gly Gln Tyr Glu Gly Asp
            20                  25                  30
Arg Gly Tyr Gly Gly Gly Tyr Lys Ser Met Met Pro Glu Ser Gly
            35                  40                  45
Pro Ser Ser Thr Gln Val Leu Ser Leu Leu Ile Gly Val Pro Val Val
    50                  55                  60
Gly Ser Leu Leu Ala Ile Ala Gly Leu Leu Leu Ala Gly Ser Val Ile
65                  70                  75                  80
Gly Ile Met Val Ala Leu Pro Leu Phe Leu Ile Phe Ser Pro Val Ile
                85                  90                  95
Val Pro Ala Gly Ile Thr Ile Gly Leu Ala Met Thr Gly Phe Ile Ala
            100                 105                 110
Ser Gly Met Phe Gly Leu Thr Gly Leu Ser Ser Ile Ser Trp Val Met
            115                 120                 125
Asn Tyr Leu Arg Gly Thr Lys Arg Thr Val Pro Glu Gln Leu Glu Tyr
        130                 135                 140
Ala Lys Arg Arg Met Ala Asp Ala Val Gly Tyr Ala Gly Gln Lys Gly
145                 150                 155                 160
Lys Glu Met Gly Gln His Val Gln Asn Lys Ala Gln Asp Val Lys Gln
                165                 170                 175
Tyr Asp Ile Ser Lys Pro His Asp Thr Thr Thr Lys Gly His Glu Thr
            180                 185                 190
Gln Gly Gly Thr Thr Ala Ala
        195

(2) INFORMATION FOR SEQ ID NO:9:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Ala Asp Thr His Arg Val Asp Arg Thr Asp Arg His Phe Gln Phe
1               5                   10                  15
Gln Ser Pro Tyr Glu Gly Gly Arg Gly Gln Gly Gln Tyr Glu Gly Asp
```

```
                   20                  25                  30
Arg Gly Tyr Gly Gly Gly Tyr Lys Ser Met Met Pro Glu Ser Gly
            35                  40                  45

Pro Ser Ser Thr Gln Val Leu Ser Leu Leu Ile Gly Val Pro Val Val
 50                      55                  60

Gly Ser Leu Ile Ala Ile Ala Gly Leu Leu Ala Gly Ser Val Ile
 65                      70              75                  80

Gly Leu Met Val Ala Leu Pro Ile Phe Leu Ile Phe Ser Pro Val Ile
                    85                  90              95

Val Pro Ala Ala Leu Thr Ile Gly Leu Ala Met Thr Gly Phe Leu Ala
                100                 105                 110

Ser Gly Met Phe Gly Leu Thr Gly Leu Ser Ser Ile Ser Trp Val Met
            115                 120                 125

Asn Tyr Leu Arg Gly Thr Arg Arg Thr Val Pro Glu Gln Leu Glu Tyr
130                 135                     140

Ala Lys Arg Arg Met Ala Asp Ala Val Gly Tyr Ala Gly Gln Lys Gly
145                     150                 155                 160

Lys Glu Met Gly Gln His Val Gln Asn Lys Ala Gln Asp Val Lys Gln
                    165                 170                 175

Tyr Asp Ile Ser Lys Pro His Asp Thr Thr Thr Lys Gly His Glu Thr
                180                     185                 190

Gln Gly Arg Thr Thr Ala Ala
            195

(2) INFORMATION FOR SEQ ID NO:10:

(i) SEQUENCE CHARACTERISTICS:
        (A) LENGTH: 1267 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

GAGCTCGATC ACACAAAGAA AACGTCAAAT GGATCATACT GGGCCCATTT TGCAGACCAA        60

GAGAAAGTGA GAGAGAGTTG TCCTCTCGTT ATCAAGTAAC AGTAGACCAC CACTAAACCG       120

CCAATAGCTT ATAATCAAAA TAGAAAGGTC TAATAACAGA AACAAATGAA AAAGCCTTGT       180

TCCATGGACT GCCTACCCGA ATTGATTGAT TCGACTAGTT TTTCTTCTTC TTTGATTAAG       240

ACCTCCGTAA GAAAATGGT ACTACTAAAG CCACTCGCTA CCAAAACTAA ACCATTCCAG        300

ACTGTAACTG GACCAATATT TCTAAACTGT AACCAGATCT CAAACATATA AACTAATTAA       360

GAACTATAAC CATTAACCGT AAAAATAAAT TTACTACAGT AAAAAATTAT ACTAATTTCA       420

GCTATGATGG AATTTCAGCT CTTAAGAGTT GTGGAAATCA AGTAAACCTA AAATCCTAAT       480

AATATTCTTC ATCCTTATTT TTGTTTCACA TGCATGCTGT CCAATCTGTT ATTAGCATTT       540

GAAAGCCTAA AATTCTATAT ACAGTACAAT AAATCTAATT AATTTTCATT ACTAATAAAA       600

TGCTTCATAT ATACTCTTGT ATTTATAAAT CATCCGTTAT CGTTACTATA CCTTTATACA       660

TCATCCTACA TTCATACCTA AGCTAGCAAA GCAAACTACT AAAAGGGTCG TCAACGCAAG       720

TTATTTGCTA GTTGGTGCAT ACTACACACG GCTACGGCAA CATTAAGTAA CACATTAAGA       780

GGTGTTTTCT TAATGTAGTA TGGTAATTAT ATTTATTTCA AAACTTGGAT TAGATATAAA       840

GGTACAGGTA GATGAAAAAT ATTTGGTTAG CGGGTTGAGA TTAAGCGGAT ATAGGAGGCA       900

TATATACAGC TGTGAGAAGA AGAGGGATAA ATACAAAAAG GGAAGGATGT TTTTGCCGAC       960
```

-continued

```
AGAGAAAGGT AGATTAAGTA GGCATCGAGA GGAGAGCAAT TGTAAAATGG ATGATTTGTT      1020

TGGTTTTGTA CGGTGGAGAG AAGAACGAAA AGATGATCAG GTAAAAAATG AAACTTGGAA      1080

ATCATGCAAA GCCACACCTC TCCCTTCAAC ACAGTCTTAC GTGTCGTCTT CTCTTCACTC      1140

CATATCTCCT TTTTATTACC AAGAAATATA TGTCAATCCC ATTTATATGT ACGTTCTCTT      1200

AGACTTATCT CTATATACCC CCTTTTAATT TGTGTGCTCT TAGCCTTTAC TCTATAGTTT      1260

TAGATAG                                                                 1267
```

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GTAATACGAC TCACTATAGG GC                                                  22
```

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GGGGATCCTA TACTAAAACT ATAGAGTAAA GG                                       32
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Trp Ile Gly His Asp Ala Gly His
1               5
```

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Asn Val Gly His Asp Ala Asn His
1               5
```

(2) INFORMATION FOR SEQ ID NO:15:

(i) SEQUENCE CHARACTERISTICS:
        (A) LENGTH: 8 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO:15:

Val Leu Gly His Asp Cys Gly His
1               5

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Val Ile Ala His Glu Cys Gly His
1               5

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Val Ile Gly His Asp Cys Ala His
1               5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Val Val Gly His Asp Cys Gly His
1               5

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

His Asn Ala His His
1               5

(2) INFORMATION FOR SEQ ID NO:20:

(i) SEQUENCE CHARACTERISTICS:
        (A) LENGTH: 6 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:20:

His Asn Tyr Leu His His
1               5

(2) INFORMATION FOR SEQ ID NO:21:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

His Arg Thr His His
1               5

(2) INFORMATION FOR SEQ ID NO:22:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

His Arg Arg His His
1               5

(2) INFORMATION FOR SEQ ID NO:23:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

His Asp Arg His His
1               5

(2) INFORMATION FOR SEQ ID NO:24:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

His Asp Gln His His
1               5

(2) INFORMATION FOR SEQ ID NO:25:

(i) SEQUENCE CHARACTERISTICS:
            (A) LENGTH: 5 amino acids
            (B) TYPE: amino acid
```

```
            (C) STRANDEDNESS: single
            (D) TOPOLOGY: linear (ii) MOLECULE TYPE: peptide (xi) SEQUENCE DESCRIPTION: SEQ ID NO:25:

His Asp His His His
1               5

(2) INFORMATION FOR SEQ ID NO:26:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:26:

His Asn His His His
1               5

(2) INFORMATION FOR SEQ ID NO:27:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:27:

Phe Gln Ile Glu His His
1               5

(2) INFORMATION FOR SEQ ID NO:28:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:28:

His Gln Val Thr His His
1               5

(2) INFORMATION FOR SEQ ID NO:29:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:29:

His Val Ile His His
1               5

(2) INFORMATION FOR SEQ ID NO:30:

(i) SEQUENCE CHARACTERISTICS:
            (A) LENGTH: 5 amino acids
            (B) TYPE: amino acid
```

(C) STRANDEDNESS: single
            (D) TOPOLOGY: linear (ii) MOLECULE TYPE: peptide (xi) SEQUENCE DESCRIPTION: SEQ ID NO:30:

His Val Ala His His
1               5

(2) INFORMATION FOR SEQ ID NO:31:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:31:

His Ile Pro His His
1               5

(2) INFORMATION FOR SEQ ID NO:32:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:32:

His Val Pro His His
1               5

(2) INFORMATION FOR SEQ ID NO:33:

(i) SEQUENCE CHARACTERISTICS:
            (A) LENGTH: 1943 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:33:

```
GAGCTCGATC ACACAAAGAA AACGTCAAAT GGATCATACT GGGCCCATTT TGCAGACCAA      60

GAGAAAGTGA GAGAGAGTTG TCCTCTCGTT ATCAAGTAAC AGTAGACCAC CACTAAACCG     120

CCAATAGCTT ATAATCAAAA TAGAAAGGTC TAATAACAGA AACAAATGAA AAAGCCTTGT     180

TCCATGGACT GCCTACCCGA ATTGATTGAT TCGACTAGTT TTTCTTCTTC TTTGATTAAG     240

ACCTCCGTAA GAAAAATGGT ACTACTAAAG CCACTCGCTA CCAAAACTAA ACCATTCCAG     300

ACTGTAACTG GACCAATATT TCTAAACTGT AACCAGATCT CAAACATATA AACTAATTAA     360

GAACTATAAC CATTAACCGT AAAAATAAAT TTACTACAGT AAAAAATTAT ACTAATTTCA     420

GCTATGATGG AATTTCAGCT CTTAAGAGTT GTGGAAATCA AGTAAACCTA AAATCCTAAT     480

AATATTCTTC ATCCTTATTT TTGTTTCACA TGCATGCTGT CCAATCTGTT ATTAGCATTT     540

GAAAGCCTAA AATTCTATAT ACAGTACAAT AAATCTAATT AATTTTCATT ACTAATAAAA     600

TGCTTCATAT ATACTCTTGT ATTTATAAAT CATCCGTTAT CGTTACTATA CCTTTATACA     660

TCATCCTACA TTCATACCTA AGCTAGCAAA GCAAACTACT AAAAGGGTCG TCAACGCAAG     720

TTATTTGCTA GTTGGTGCAT ACTACACACG GCTACGGCAA CATTAAGTAA CACATTAAGA     780
```

```
GGTGTTTTCT TAATGTAGTA TGGTAATTAT ATTTATTTCA AAACTTGGAT TAGATATAAA      840

GGTACAGGTA GATGAAAAAT ATTTGGTTAG CGGGTTGAGA TTAAGCGGAT ATAGGAGGCA      900

TATATACAGC TGTGAGAAGA AGAGGGATAA ATACAAAAAG GGAAGGATGT TTTTGCCGAC      960

AGAGAAAGGT AGATTAAGTA GGCATCGAGA GGAGAGCAAT TGTAAAATGG ATGATTTGTT     1020

TGGTTTTGTA CGGTGGAGAG AAGAACGAAA AGATGATCAG GTAAAAAATG AAACTTGGAA     1080

ATCATGCAAA GCCACACCTC TCCCTTCAAC ACAGTCTTAC GTGTCGTCTT CTCTTCACTC     1140

CATATCTCCT TTTTATTACC AAGAAATATA TGTCAATCCC ATTTATATGT ACGTTCTCTT     1200

AGACTTATCT CTATATACCC CCTTTTAATT TGTGTGCTCT TAGCCTTTAC TCTATAGTTT     1260

TAGATAGACA TGGCGAATGT GGATCGTGAT CGGCGTGTGC ATGTAGACCG TACTGACAAA     1320

CGTGTTCATC AGCCAAACTA CGAAGATGAT GTCGGTTTTG GTGGCTATGG CGGTTATGGT     1380

GCTGGTTCTG ATTATAAGAG TCGCGGCCCC TCCACTAACC AAGTATTTTT GTGGTCTCTT     1440

TAGTTTTTCT TGTGTTTTCC TATGATCACG CTCTCCAAAC TATTTGAAGA TTTTCTGTAA     1500

ATTCATTTTA AACAGAAAGA TAAATAAAAT AGTGAAGAAC CATAGGAATC GTACGTTACG     1560

TTAATTATTT CCTTTTAGTT CTTAAGTCCT AATTAGGATT CCTTTAAAAG TTGCAACAAT     1620

CTAATTGTTC ACAAAATGAG TAAAGTTTGA AACAGATTTT TATACACCAC TTGCATATGT     1680

TTATCATGGT GATGCATGCT TGTTAGATAA ACTCGATATA ATCAATACAT GCAGATCTTG     1740

GCACTTATAG CAGGAGTTCC CATTGGTGGC ACACTGCTAA CCCTAGCTGG ACTCACTCTA     1800

GCCGGTTCGG TGATCGGCTT GCTAGTCTCC ATACCCCTCT TCCTCCTCTT CAGTCCGGTG     1860

ATAGTCCCGG CGGCTCTCAC TATTGGGCTT GCTGTGACGG GAATCTTGGC TTCTGGTTTG     1920

TTTGGGTTGA CGGGTCTGAG CTC                                            1943
```